US011512357B2

United States Patent
Moore et al.

(10) Patent No.: US 11,512,357 B2
(45) Date of Patent: Nov. 29, 2022

(54) GAMMA HERPESVIRUS CIRCULAR RNA

(71) Applicant: University of Pittsburgh—Of the Commonwealth System of Higher Education, Pittsburgh, PA (US)

(72) Inventors: Patrick S. Moore, Pittsburgh, PA (US); Tuna Toptan, Pittsburgh, PA (US); Yuan Chang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/059,949

(22) PCT Filed: May 31, 2019

(86) PCT No.: PCT/US2019/034995
§ 371 (c)(1),
(2) Date: Nov. 30, 2020

(87) PCT Pub. No.: WO2019/232436
PCT Pub. Date: Dec. 5, 2019

(65) Prior Publication Data
US 2021/0207228 A1    Jul. 8, 2021

Related U.S. Application Data

(60) Provisional application No. 62/679,712, filed on Jun. 1, 2018, provisional application No. 62/679,698, filed
(Continued)

(51) Int. Cl.
| C12Q 1/70 | (2006.01) |
| C12N 15/113 | (2010.01) |
| A61K 48/00 | (2006.01) |

(52) U.S. Cl.
CPC .......... *C12Q 1/705* (2013.01); *C12N 15/1133* (2013.01); *A61K 48/00* (2013.01); *C12N 2310/315* (2013.01); *C12N 2310/321* (2013.01)

(58) Field of Classification Search
CPC ............ A61K 48/00; C12N 2310/315; C12N 2310/321; C12N 15/1133; C12Q 1/705
See application file for complete search history.

(56) References Cited

U.S. PATENT DOCUMENTS

| 2004/0005551 A1 | 1/2004 | Lo et al. |
| 2006/0104956 A1 | 5/2006 | Satishchandran et al. |
(Continued)

OTHER PUBLICATIONS

International Searching Authority, Written Opinion in International Patent Application No. PCT/US2019/034995, dated Nov. 8, 2019.
(Continued)

*Primary Examiner* — Terra C Gibbs
(74) *Attorney, Agent, or Firm* — Leydig, Voit & Mayer

(57) ABSTRACT

In an embodiment, the invention provides a method and reagents for detection of γ-herpesvirus circRNA. In another embodiment, the invention provides a method and reagents for detection of EBV circRNA. In still another embodiment, the invention provides a method and reagents for detection of KSHV circRNA. The method can be expanded to other herpesviruses and even non-herpesviruses that generate circRNA upon cellular infection.

22 Claims, 9 Drawing Sheets
Specification includes a Sequence Listing.

Related U.S. Application Data on Jun. 1, 2018, provisional application No. 62/679,725, filed on Jun. 1, 2018.

(56) References Cited

U.S. PATENT DOCUMENTS

| | | |
|---|---|---|
| 2016/0194368 A1 | 7/2016 | Hoge et al. |
| 2018/0023079 A1 | 1/2018 | Dimmeler et al. |
| 2018/0282809 A1* | 10/2018 | Rajewsky ............ C12Q 1/6883 |

OTHER PUBLICATIONS

International Searching Authority, International Search Report in International Patent Application No. PCT/US2019/034995, dated Nov. 8, 2019.

Riese, "Identification of Potential Viral Circular RNA in Epstein Barr Virus-Producing Cells," Fall 2015 Honors Projects and Posters, Iowa State University Digital Repository (Dec. 2015).

Toptan et al., "Circular DNA tumor viruses make circular RNAs," *PNAS*, 115(37):E8737-E8745 (2018).

* cited by examiner circBART-akata 711nuc:

Atgccattgggcgtgtcactgagctgaatttggacgcagctacttgacctttgcccccgtgcctccagcgctgataagtgct
gcgtccactttgtgttacaggtccggcgtgtccacggagactcggacgtagcccttaccgcggcgtatggcgttgaccggacataccttc
ccccgggaatgtgtgaatacgggcgtatgactttagaaatgggggcgtgtgctgcgccagcaggtaaggcaggcactcgtcctggct
ggtgacgggagagccactgaggaagatctggggctcgctggtgtttagcttgtccccgctctgggtgcaggagcgtgtcagctgaat
gtcgctctgcccgggcagaatctgcaggtagaggtaggggttcttgaccaatctgatgggcacaatgtaccaggtaaacttccctttctc
tatgaacaggctgcgcggattcaggacgcttagcacgatgtcctggtcagagtgcataacgaagaagggcttgaggaatacctcgttg
tcttccgctccaaagaacaaaaacgcgaccgtaaagtagcggctgccgtaggtggtcgtgttgaaggagaaagaagtgggccgcag
gcggcggaggctgttcctgaacgacgagcgccgggacgctagtgctgcatgggctcctccggggtaagcttcggccatggccgga
gctcgtcgacgggcaag (SEQ ID NO:16)

FIG. 2A

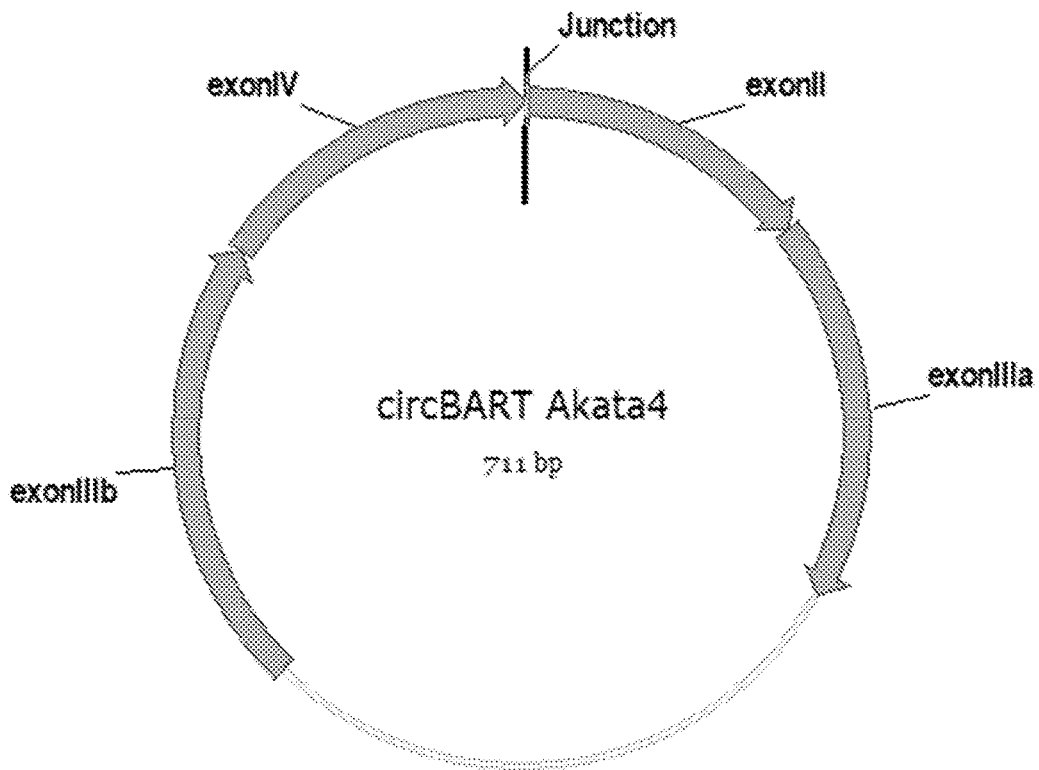

FIG. 2B circRPMS1-akata 609nuc:

gtccggcgtgtccacggagactcggacgtagcccttaccgcggcgtatggcgttgaccggacataccttccccgggaatgtgtgaat
acgggcgtatgactttagaaatgggggcgtgtgctgcgccagcaggtaaggcaggcactcgtcctggctggtgacgggagagccac
tgaggaagatctggggctcgctggtgtttagcttgtccccgctctgggtgcaggagcgtgtcagctgaatgtcgctctgcccgggcag
aatctgcaggtagaggtaggggttcttgaccaatctgatgggcacaatgtaccaggtaaacttcccttctctatgaacaggctgcgcgg
attcaggacgcttagcacgatgtcctggtcagagtgcataacgaagaagggcttgaggaatacctcgttgtcttccgctccaaagaaca
aaaacgcgaccgtaaagtagcggctgccgtaggtggtcgtgttgaaggagaaagaagtgggccgcaggcggcggaggctgttcct
gaacgacgagcgccgggacgctagtgctgcatgggctcctccggggtaagcttcggccatggccggagctcgtcgacgggcaag
(SEQ ID NO:17)

FIG. 3A

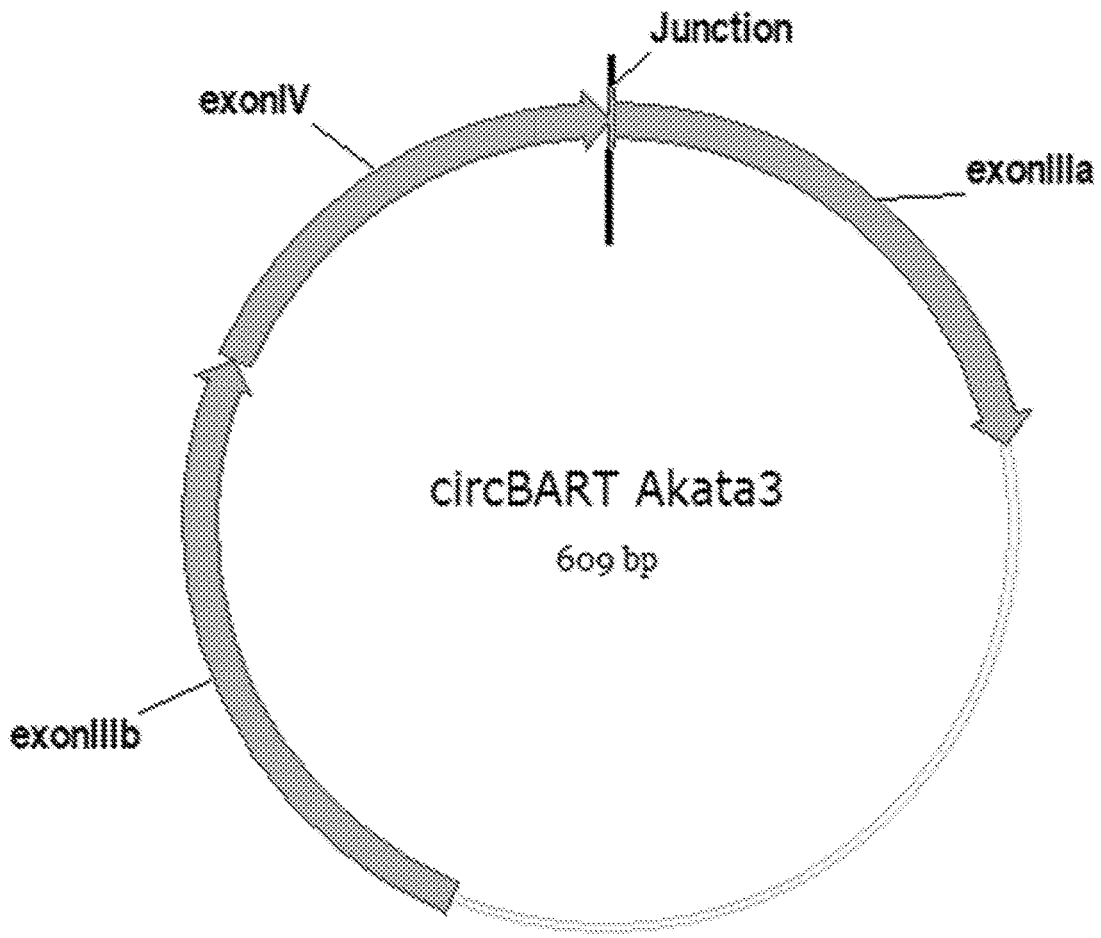

FIG. 3B circRPMS1-akata 501nuc:

atgccgttgaacgtgtcactgagctgaatttggtcgcagctacttgacctttgccccgtgcctccagcgctgataagtgctgcgtccact
ttgtgttacaggtccggcgtgtccacggagactcggacgtagcccttaccgcggcgtatggcgttgaccggacataccttccccggga
atgtgtgaatacgggcgtatgactttagaaatgggggcgtgtgctgcgccagcaggctgcgcggattcaggacgcttagcacgatgtc
ctggtcagagtgcataacgaagaagggcttgaggaatacctcgttgtcttccgctccaaagaacaaaaacgcgaccgtaaagtagcg
gctgccgtaggtggtcgtgttgaaggagaaagaagtgggccgcaggcggcggaggctgttcctgaacgacgagcgccgggacgc
tagtgctgcatgggctcctccggggtaagcttcggccatggccggagctcgtcgacgggcaag (SEQ ID NO:18)

FIG. 4A

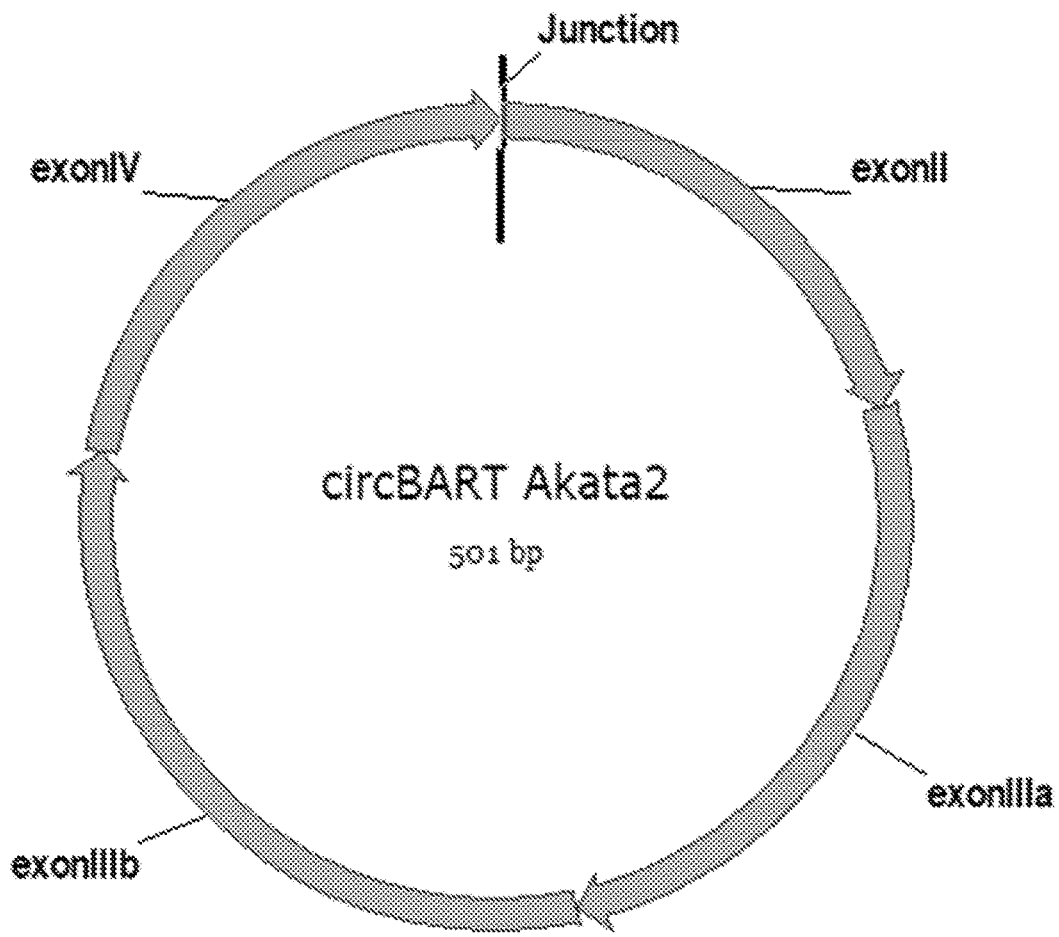

FIG. 4B circRPMS1-akata 399nuc:

Gtccggcgtgtccacggagactcggacgtagcccttaccgcggcgtatggcgttgaccggacataccttccccgggaatgtgtgaatacgggcgtatgactttagaaatggggggcgtgtgctgcgccagcaggctgcgcggattcaggacgcttagcacgatgtcctggtcagagtgcataacgaagaagggcttgaggaatacctcgttgtcttccgctccaaagaacaaaaacgcgaccgtaaagtagcggctgccgtaggtggtcgtgttgaaggagaaagaagtgggccgcaggcggcggaggctgttcctgaacgacgagcgccgggacgctagtgctgcatgggctcctccggggtaagcttcggccatggccggagctcgtcgacgggcaag (SEQ ID NO:19).

FIG. 5A

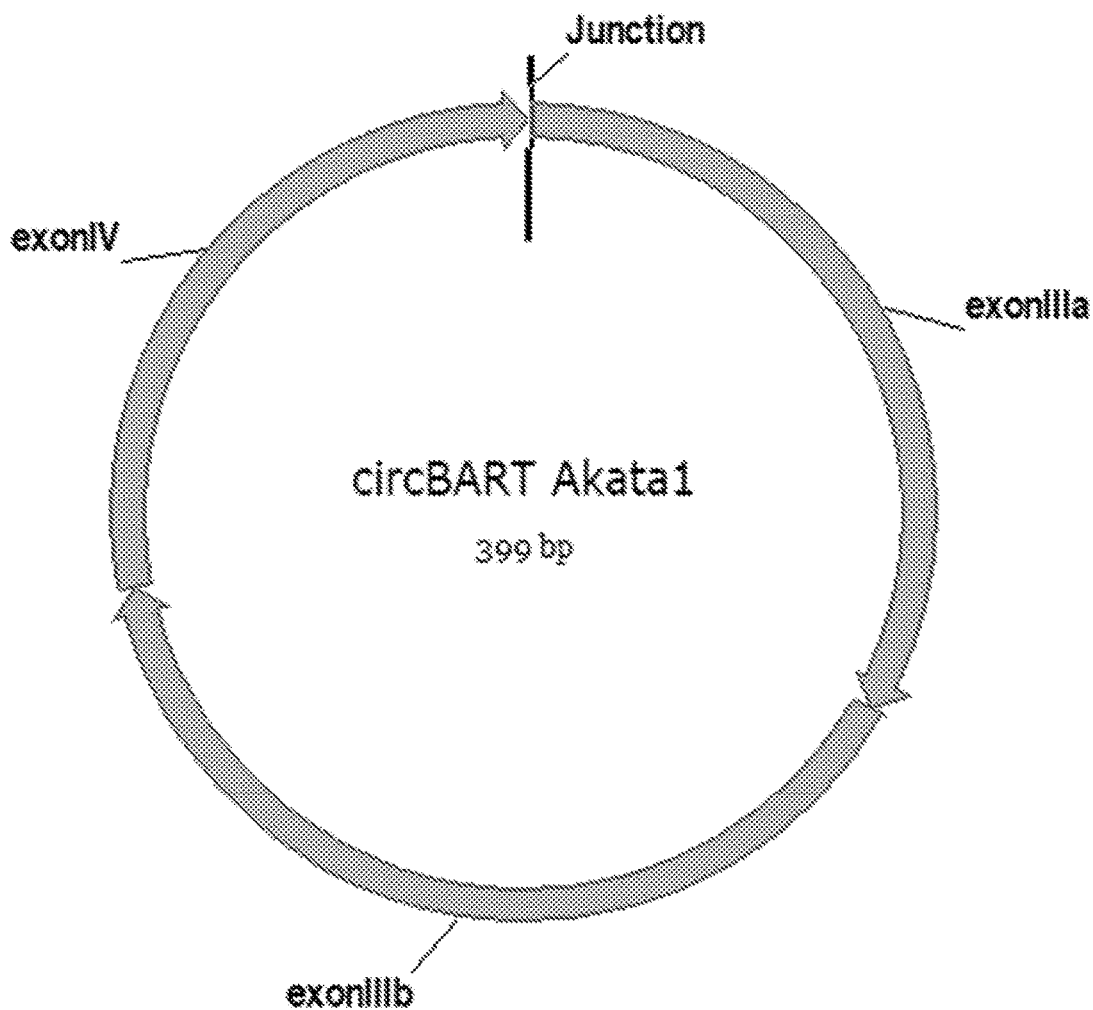

FIG. 5B

KSHV circ-vIRF4

Gtgtggataccagtgaatgagggcgcatctacctcagcccccgcgcccctgcctgccggcagcgatatcccgcctggctggtattcggtgtaccatgcatttgatgaggagtgtgatagagtctacggaccatcgcctgtcgtgggacagacggtgtatggacgttttgggagactgttgcgtggaaccaggagggccgtcgtgcggaacgatttacggtacagcgacacatttggtggtagctacgtagtatggcagttggtgcgaacgccgtttaaaaactgtacgtattgctatggggccgcgtatggtcctgaaaaactgcagcgatttattcagtgtctgttgtccccccaatgcaaaccacggctacgcgacgcagtgacactaggtatgtaactcggggaaggggtgtgaggtttgatgcgttggtgtcggcgggaaatactttaggtaccctaaccacgttaactctcgtgccttttacttagagaacaaagctacgaggaggcaggggctgcagcacctgctccccctaaggcgccatcggggctgaggggtcgccctcggaaatcgaaccgctattacaatgttggcgatataacgactgaacagaaggctgcctgctcc (SEQ ID NO:20)

FIG. 6A

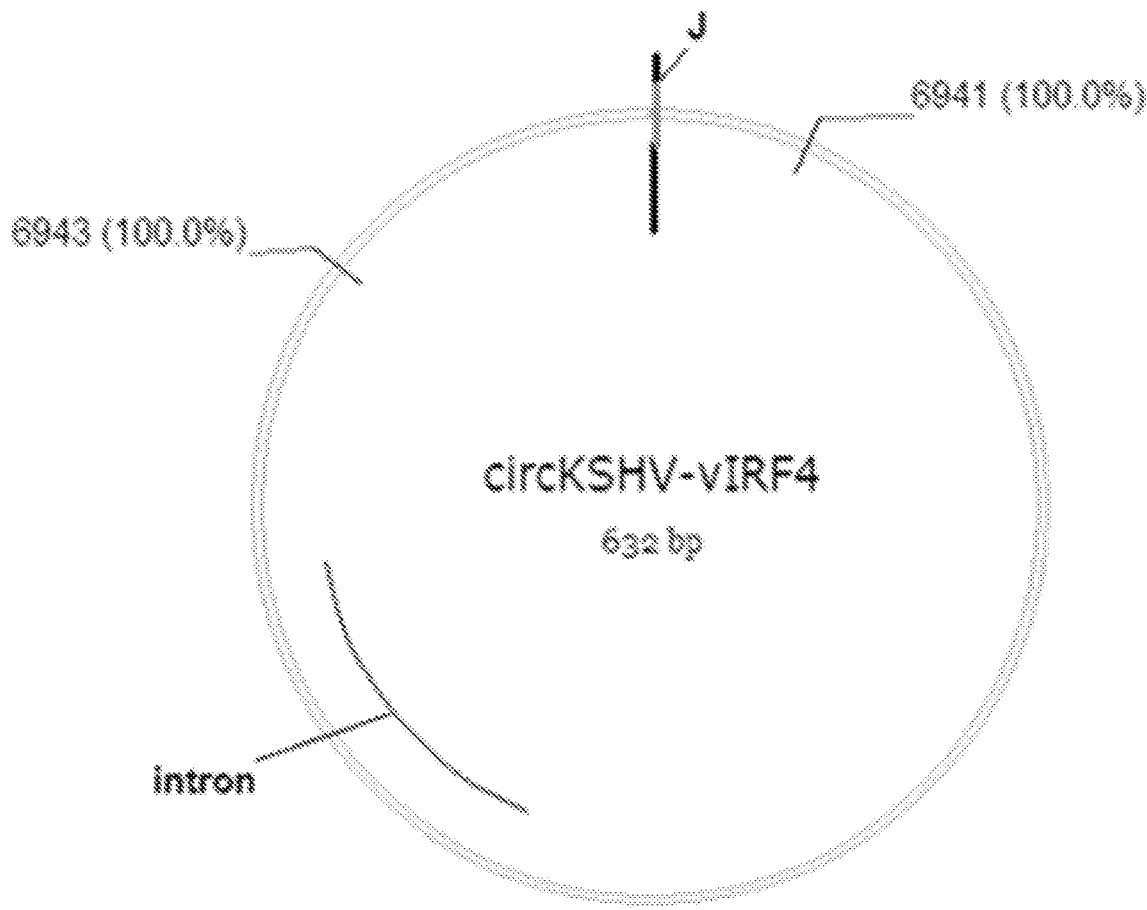

FIG. 6B circPAN(-) 28692-29016

Gctgccgcacaccactttagtccaatgttcttacacgactttgaaacttctgacaaatgccacctcactttgtcgcctatgtcattcaaatcgacttgcttacactggaaaaataaacacaccattacagcactagcctgatacaatctaaaacgcattttaaaatgcttcacaacgcaccaataagatacacatccagattgtcacatttagggcaaagtggcccgatttacactcaatccgctttctagaattacctcaacactatctaagaatcagacaaacacagaaccgaaacaacgaatgagcagatagagcgctccca (SEQ ID NO:21)

FIG. 7A circPAN(-) 28519-29016 gctgccgcacaccactttagtccaatgttcttacacgactttgaaacttctgacaaatgccacctcactttgtcgcctatgtcattcaaatcgacttgcttacactggaaaaataaacacaccattacagcactagcctgatacaatctaaaacgcattttaaaatgcttcacaacgcaccaataagatacacatccagattgtcacatttagggcaaagtggcccgatttacactcaatccgctttctagaattacctcaacactatctaagaatcagacaaacacagaaccgaaacaacgaatgagcagataggtagtgcaccactgttctgatacaccagtgggcgctgctttcctttcacattatattccacattcagacacgttaagtatcctcgcatatcataaaggggctacaactggcctggagattgaatccaatgcaataacccgcaaggggtgactgtatagttgccatggcaagagcgctccca(SEQ ID NO:22)

FIG. 7B circPAN(-) 28420-28717 acgaatgagcagataggtagtgcaccactgttctgatacaccagtgggcgctgctttcctttcacattatattccacattcagacacgttaagtatcctcgcatatcataaaggggctacaactggcctggagattgaatccaatgcaataacccgcaaggggtgactgtatagttgccatggcaaggttttgggcaaatcgcagcttttgttctgcgggcttatggagagctccagaccgcgcggtgttttttgtactacagctctcaggccaatgtgggaaaaaaccgaaaca (SEQ ID NO:23)

FIG. 7C circPAN(-)28290-28691 actgttctgatacaccagtgggcgctgctttcctttcacattatattccacattcagacacgttaagtatcctcgcatatcataaaggggggctacaactggcctggagattgaatccaatgcaataacccgcaaggggtgactgtatagttgccatggcaaggttttgggcaaatcgcagcttttgttctgcgggcttatggagagctccagaccgcgcggtgttttttgtactacagctctcaggccaatgtgggaaaagtaggacggaaaacctagccgaaagccaggatgggtatattgccaaaagcgacgcaatcaacccacaatcggcggcaccaatgaaaaccagaagcggcaagaaggcaagcagcgagcacaaaatccataggtagtgcacc (SEQ ID NO:24)

FIG. 7D circPAN(-) 28290-28593 ctggcctggagattgaatccaatgcaataacccgcaaggggtgactgtatagttgccatggcaaggttttgggcaaatcgc
agcttttgttctgcgggcttatggagagctccagaccgcgcggtgttttttgtactacagctctcaggccaatgtgggaaaagtaggacg
gaaaacctagccgaaagccaggatgggtatattgccaaaagcgacgcaatcaacccacaatcggcggcaccaatgaaaaccagaa
gcggcaagaaggcaagcagcgagcacaaaatcatagggggctacaa (SEQ ID NO:25)

FIG. 7E circPAN(+) 28406-29099 ctacttttcccacattggcctgagagctgtagtacaaaaaacaccgcgcggtctggagctctccataagcccgcagaacaa
aagctgcgatttgcccaaaaaccttgccatggcaactatacagtcaccccttgcgggttattgcattggattcaatctccaggccagttgt
agccccctttatgatatgcgaggatacttaacgtgtctgaatgtggaatataatgtgaaaggaaagcagcgcccactggtgtatcagaa
cagtggtgcactacctatctgctcattcgttgtttcggttctgtgtttgtctgattcttagatagtgttgaggtaattctagaaagcggattgag
tgtaaatcgggccactttgccctaaatgtgacaatctggatgtgtatcttattggtgcgttgtgaagcattttaaaatgcgttttagattgtatc
aggctagtgctgtaatggtgtgtttattttccagtgtaagcaagtcgatttgaatgacataggcgacaaagtgaggtggcatttgtcagaa
gtttcaaagtcgtgtaagaacattggactaaagtggtgtgcggcagctgggagcgctctttcaatgttaatgttttaatgtgtatgttgtgtt
ggaagttccaggctaatatttgatgttttgctaggttgactaacgatgttttccgtc (SEQ ID NO:26)

FIG. 7F circPAN(+) 28406-28888 ctacttttcccacattggcctgagagctgtagtacaaaaaacaccgcgcggtctggagctctccataagcccgcagaacaa
aagctgcgatttgcccaaaaaccttgccatggcaactatacagtcaccccttgcgggttattgcattggattcaatctccaggccagttgt
agccccctttatgatatgcgaggatacttaacgtgtctgaatgtggaatataatgtgaaaggaaagcagcgcccactggtgtatcagaa
cagtggtgcactacctatctgctcattcgttgtttcggttctgtgtttgtctgattcttagatagtgttgaggtaattctagaaagcggattgag
tgtaaatcgggccactttgccctaaatgtgacaatctggatgtgtatcttattggtgcgttgtgaagcattttaaaatgcgttttagattgtatc
aggctagtgctgtaatggtgtgttttccgtc (SEQ ID NO:27)

FIG. 7G circPAN(+) 28406-28721 ctacttttcccacattggcctgagagctgtagtacaaaaaacaccgcgcggtctggagctctccataagcccgcagaacaaaagctgcgatttgcccaaaaaccttgccatggcaactatacagtcaccccttgcgggttattgcattggattcaatctccaggccagttgtagccccctttttatgatatgcgaggatacttaacgtgtctgaatgtggaatataatgtgaaaggaaagcagcgcccactggtgtatcagaacagtggtgcactacctatctgctcattcgttgtttcggttctgtgttttccgtc (SEQ ID NO:28)

FIG. 7H circPAN(+) 28406-28708 ctacttttcccacattggcctgagagctgtagtacaaaaaacaccgcgcggtctggagctctccataagcccgcagaacaaaagctgcgatttgcccaaaaaccttgccatggcaactatacagtcaccccttgcgggttattgcattggattcaatctccaggccagttgtagccccctttttatgatatgcgaggatacttaacgtgtctgaatgtggaatataatgtgaaaggaaagcagcgcccactggtgtatcagaacagtggtgcactacctatctgctcattcgttgttttccgtc (SEQ ID NO:29)

FIG. 7I

SEQUENCE LISTING

<160> NUMBER OF SEQ ID NOS: 76

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
cgcccgtatt cacacattcc                    20

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
gacgctagtg ctgcatggg                     19

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
tgaggaatac ctcgttgtct tccg                                  24

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
agcccttctt cgttatgcac                                       20

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
caaatgcatg gtacaccgaa tac                                   23

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
gaaccgctat tacaatgttg gc                                    22

<210> SEQ ID NO 7
<211> LENGTH: 24
<212> TYPE: DNA
<213> ORGANISM: Artificial Sequence
<220> FEATURE:
<223> OTHER INFORMATION: Sythentic

<400> SEQUENCE: 7
tcgacgggca aggtccggcg tgtc                                  24

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
tcgacgggca agatgccatt gggc                                  24

<210> SEQ ID NO 9
<211> LENGTH: 24
<212> TYPE: DNA
<213> ORGANISM: Artificial Sequence

```
<220> FEATURE:
<223> OTHER INFORMATION: Synthetic

<400> SEQUENCE: 9
gacacgccgg accttgcccg ucga                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
agccucgacc gtgaccgtgc agcc                                              24

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
gcccaatggc atcttgcccg ucga                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
agucgtctcg tcacgcaggc cuac                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
catctacctc agcccccgcg cccc                                              24

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
ggggcgcggg ggctgaggua gaug                                              24

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
ggcggugcgg cgtgaggaag gugg                                              24
```

<210> SEQ ID NO 16
<211> LENGTH: 711
<212> TYPE: DNA
<213> ORGANISM: Artificial Sequence
<220> FEATURE:
<223> OTHER INFORMATION: Synthetic

<400> SEQUENCE: 16

```
atgccattgg gcgtgtcact gagctgaatt tggacgcagc tacttgacct ttgccccgt      60
gcctccagcg ctgataagtg ctgcgtccac tttgtgttac aggtccggcg tgtccacgga     120
gactcggacg tagcccttac cgcggcgtat ggcgttgacc ggacataccct tccccgggaa    180
tgtgtgaata cgggcgtatg actttagaaa tggggcgtg tgctgcgcca gcaggtaagg      240
caggcactcg tcctggctgg tgacgggaga gccactgagg aagatctggg gctcgctggt     300
gtttagcttg tccccgctct gggtgcagga gcgtgtcagc tgaatgtcgc tctgcccggg     360
cagaatctgc aggtagaggt aggggttctt gaccaatctg atgggcacaa tgtaccaggt     420
aaacttccct ttctctatga acaggctgcg cggattcagg acgcttagca cgatgtcctg     480
gtcagagtgc ataacgaaga agggcttgag gaatacctcg ttgtcttccg ctccaaagaa     540
caaaaacgcg accgtaaagt agcggctgcc gtaggtggtc gtgttgaagg agaaagaagt     600
gggccgcagg cggcggaggc tgttcctgaa cgacgagcgc cgggacgcta gtgctgcatg     660
ggctcctccg ggtaagcttc ggccatggc cggagctcgt cgacgggcaa g               711
```

<210> SEQ ID NO 17
<211> LENGTH: 609
<212> TYPE: DNA
<213> ORGANISM: Artificial Sequence
<220> FEATURE:
<223> OTHER INFORMATION: Synthetic

<400> SEQUENCE: 17

```
gtccggcgtg tccacggaga ctcggacgta gcccttaccg cggcgtatgg cgttgaccgg      60
acataccttc cccgggaatg tgtgaatacg ggcgtatgac tttagaaatg ggggcgtgtg    120
ctgcgccagc aggtaaggca ggcactcgtc ctggctggtg acgggagagc cactgaggaa    180
gatctggggc tcgctggtgt ttagcttgtc cccgctctgg gtgcaggagc gtgtcagctg    240
aatgtcgctc tgcccgggca gaatctgcag gtagaggtag gggttcttga ccaatctgat    300
gggcacaatg taccaggtaa acttcccttt ctctatgaac aggctgcgcg gattcaggac    360
gcttagcacg atgtcctggt cagagtgcat aacgaagaag ggcttgagga atacctcgtt    420
gtcttccgct ccaaagaaca aaaacgcgac cgtaaagtag cggctgccgt aggtggtcgt    480
gttgaaggag aaagaagtgg gccgcaggcg gcggaggctg ttcctgaacg acgagcgccg    540
gacgctagt gctgcatggg ctcctccggg gtaagcttcg gccatggccg gagctcgtcg    600
acgggcaag                                                             609
```

<210> SEQ ID NO 18
<211> LENGTH: 501
<212> TYPE: DNA
<213> ORGANISM: Artificial Sequence
<220> FEATURE:
<223> OTHER INFORMATION: Synthetic

<400> SEQUENCE: 18

```
atgccgttga acgtgtcact gagctgaatt tggtcgcagc tacttgacct ttgccccgt      60
gcctccagcg ctgataagtg ctgcgtccac tttgtgttac aggtccggcg tgtccacgga    120
```

```
gactcggacg tagcccttac cgcggcgtat ggcgttgacc ggacatacct tccccgggaa    180
tgtgtgaata cgggcgtatg actttagaaa tggggcgtg tgctgcgcca gcaggctgcg     240
cggattcagg acgcttagca cgatgtcctg gtcagagtgc ataacgaaga agggcttgag    300
gaatacctcg ttgtcttccg ctccaaagaa caaaaacgcg accgtaaagt agcggctgcc    360
gtaggtggtc gtgttgaagg agaaagaagt gggccgcagg cggcggaggc tgttcctgaa    420
cgacgagcgc cggacgcta gtgctgcatg ggctcctccg ggtaagcttc ggccatggc     480 cggagctcgt cgacgggcaa g                                              501

<210> SEQ ID NO 19
<211> LENGTH: 399
<212> TYPE: DNA
<213> ORGANISM: Artificial Sequence
<220> FEATURE:
<223> OTHER INFORMATION: Synthetic

<400> SEQUENCE: 19
gtccggcgtg tccacggaga ctcggacgta gcccttaccg cggcgtatgg cgttgaccgg     60
acataccttc cccgggaatg tgtgaatacg ggcgtatgac tttagaaatg ggggcgtgtg    120
ctgcgccagc aggctgcgcg gattcaggac gcttagcacg atgtcctggt cagagtgcat    180
aacgaagaag ggcttgagga atacctcgtt gtcttccgct ccaaagaaca aaaacgcgac    240
cgtaaagtag cggctgccgt aggtggtcgt gttgaaggag aaagaagtgg gccgcaggcg    300
gcggaggctg ttcctgaacg acgagcgccg gacgctagt gctgcatggg ctcctccggg    360
gtaagcttcg gccatggccg gagctcgtcg acgggcaag                           399

<210> SEQ ID NO 20
<211> LENGTH: 632
<212> TYPE: DNA
<213> ORGANISM: Artificial Sequence
<220> FEATURE:
<223> OTHER INFORMATION: Synthetic

<400> SEQUENCE: 20
gtgtggatac cagtgaatga gggcgcatct acctcagccc ccgcgcccct gcctgccggc     60
agcgatatcc cgcctggctg gtattcggtg taccatgcat tgatgagga gtgtgataga    120 gtctacggac catcgcctgt cgtgggacag acggtatatg gacgttttgg gagactgttg    180
cgtggaacca ggagggccgt cgtgcggaac gatttacggt acagcgacac atttggtggt    240
agctacgtag tatggcagtt ggtgcgaacg ccgtttaaaa actgtacgta ttgctatggg    300
gccgcgtatg gtcctgaaaa actgcagcga tttattcagt gtctgttgtc cccccaatg    360 caaaccacgg ctacgcgacg cagtgacact aggtatgtaa ctcggggaag ggggtgtgag    420
gtttgatgcg ttggtgtcgg cgggaaatac tttaggtacc ctaaccacgt taactctcgt    480 gcctttact tagagaacaa agctacgagg aggcagggc tgcagcacct gctcccccta    540
aggcgccatc ggggctgagg ggtcgccctc ggaaatcgaa ccgctattac aatgttggcg    600
atataacgac tgaacagaag gctgcctgct cc                                  632

<210> SEQ ID NO 21
<211> LENGTH: 325
<212> TYPE: DNA
<213> ORGANISM: Artificial Sequence
<220> FEATURE:
<223> OTHER INFORMATION: Synthetic
```

<400> SEQUENCE: 21

```
gctgccgcac accactttag tccaatgttc ttacacgact ttgaaacttc tgacaaatgc      60
cacctcactt tgtcgcctat gtcattcaaa tcgacttgct tacactggaa aaataaacac     120
accattacag cactagcctg atacaatcta aaacgcattt taaaatgctt cacaacgcac     180
caataagata cacatccaga ttgtcacatt tagggcaaag tggcccgatt tacactcaat     240
ccgctttcta gaattacctc aacactatct aagaatcaga caaacacaga accgaaacaa     300
cgaatgagca gatagagcgc tccca                                           325
```

<210> SEQ ID NO 22
<211> LENGTH: 498
<212> TYPE: DNA
<213> ORGANISM: Artificial Sequence
<220> FEATURE:
<223> OTHER INFORMATION: Synthetic

<400> SEQUENCE: 22

```
gctgccgcac accactttag tccaatgttc ttacacgact ttgaaacttc tgacaaatgc      60
cacctcactt tgtcgcctat gtcattcaaa tcgacttgct tacactggaa aaataaacac     120
accattacag cactagcctg atacaatcta aaacgcattt taaaatgctt cacaacgcac     180
caataagata cacatccaga ttgtcacatt tagggcaaag tggcccgatt tacactcaat     240
ccgctttcta gaattacctc aacactatct aagaatcaga caaacacaga accgaaacaa     300
cgaatgagca gataggtagt gcaccactgt tctgatacac cagtgggcgc tgctttcctt     360
tcacattata ttccacattc agacacgtta agtatcctcg catatcataa aaggggcta     420
caactggcct ggagattgaa tccaatgcaa taacccgcaa ggggtgactg tatagttgcc     480
atggcaagag cgctccca                                                   498
```

<210> SEQ ID NO 23
<211> LENGTH: 298
<212> TYPE: DNA
<213> ORGANISM: Artificial Sequence
<220> FEATURE:
<223> OTHER INFORMATION: Synthetic

<400> SEQUENCE: 23

```
acgaatgagc agataggtag tgcaccactg ttctgataca ccagtgggcg ctgctttcct      60
ttcacattat attccacatt cagacacgtt aagtatcctc gcatatcata aaaggggct     120
acaactggcc tggagattga atccaatgca ataacccgca aggggtgact gtatagttgc     180
catggcaagg ttttgggca atcgcagct tttgttctgc gggcttatgg agagctccag     240
accgcgcggt gttttttgta ctacagctct caggccaatg tgggaaaaaa ccgaaaca      298
```

<210> SEQ ID NO 24
<211> LENGTH: 402
<212> TYPE: DNA
<213> ORGANISM: Artificial Sequence
<220> FEATURE:
<223> OTHER INFORMATION: Synthetic

<400> SEQUENCE: 24

```
actgttctga tacaccagtg ggcgctgctt tcctttcaca ttatattcca cattcagaca      60
cgttaagtat cctcgcatat cataaaaggg ggctacaact ggcctggaga ttgaatccaa    120
tgcaataacc cgcaagggt gactgtatag ttgccatggc aaggttttg ggcaaatcgc     180
agcttttgtt ctgcgggctt atggagagct ccagaccgcg cggtgttttt tgtactacag    240
```

```
ctctcaggcc aatgtgggaa aagtaggacg gaaaacctag ccgaaagcca ggatgggtat    300
attgccaaaa gcgacgcaat caacccacaa tcggcggcac caatgaaaac cagaagcggc    360
aagaaggcaa gcagcgagca caaaatccat aggtagtgca cc                      402
```

```
<210> SEQ ID NO 25
<211> LENGTH: 304
<212> TYPE: DNA
<213> ORGANISM: Artificial Sequence
<220> FEATURE:
<223> OTHER INFORMATION: Synthetic

<400> SEQUENCE: 25
ctggcctgga gattgaatcc aatgcaataa cccgcaaggg gtgactgtat agttgccatg     60
gcaaggtttt tgggcaaatc gcagcttttg ttctgcgggc ttatggagag ctccagaccg    120
cgcggtgttt tttgtactac agctctcagg ccaatgtggg aaaagtagga cggaaaacct    180
agccgaaagc caggatgggt atattgccaa aagcgacgca atcaacccac aatcggcggc    240
accaatgaaa accagaagcg gcaagaaggc aagcagcgag cacaaaatcc ataggggct    300 acaa                                                                304
```

```
<210> SEQ ID NO 26
<211> LENGTH: 694
<212> TYPE: DNA
<213> ORGANISM: Artificial Sequence
<220> FEATURE:
<223> OTHER INFORMATION: Synthetic

<400> SEQUENCE: 26
ctacttttcc cacattggcc tgagagctgt agtacaaaaa acaccgcgcg gtctggagct     60
ctccataagc ccgcagaaca aaagctgcga tttgcccaaa aaccttgcca tggcaactat    120
acagtcaccc cttgcgggtt attgcattgg attcaatctc caggccagtt gtagcccct    180 tttatgatat gcgaggatac ttaacgtgtc tgaatgtgga atataatgtg aaaggaaagc    240
agcgcccact ggtgtatcag aacagtggtg cactacctat ctgctcattc gttgtttcgg    300
ttctgtgttt gtctgattct agatagtgt tgaggtaatt ctagaaagcg gattgagtgt    360
aaatcgggcc actttgccct aaatgtgaca atctggatgt gtatcttatt ggtgcgttgt    420
gaagcatttt aaaatgcgtt ttagattgta tcaggctagt gctgtaatgg tgtgtttatt    480
tttccagtgt aagcaagtcg atttgaatga cataggcgac aaagtgaggt ggcatttgtc    540
agaagtttca aagtcgtgta agaacattgg actaaagtgg tgtgcggcag ctgggagcgc    600
tctttcaatg ttaatgtttt aatgtgtatg ttgtgttgga agttccaggc taatatttga    660
tgttttgcta ggttgactaa cgatgttttc cgtc                               694
```

```
<210> SEQ ID NO 27
<211> LENGTH: 483
<212> TYPE: DNA
<213> ORGANISM: Artificial Sequence
<220> FEATURE:
<223> OTHER INFORMATION: Synthetic

<400> SEQUENCE: 27
ctacttttcc cacattggcc tgagagctgt agtacaaaaa acaccgcgcg gtctggagct     60
ctccataagc ccgcagaaca aaagctgcga tttgcccaaa aaccttgcca tggcaactat    120
acagtcaccc cttgcgggtt attgcattgg attcaatctc caggccagtt gtagcccct    180 tttatgatat gcgaggatac ttaacgtgtc tgaatgtgga atataatgtg aaaggaaagc    240
```

```
agcgcccact ggtgtatcag aacagtggtg cactacctat ctgctcattc gttgtttcgg    300
ttctgtgttt gtctgattct tagatagtgt tgaggtaatt ctagaaagcg gattgagtgt    360
aaatcgggcc actttgccct aaatgtgaca atctggatgt gtatcttatt ggtgcgttgt    420
gaagcatttt aaaatgcgtt ttagattgta tcaggctagt gctgtaatgg tgtgttttcc    480
gtc                                                                  483

<210> SEQ ID NO 28
<211> LENGTH: 316
<212> TYPE: DNA
<213> ORGANISM: Artificial Sequence
<220> FEATURE:
<223> OTHER INFORMATION: Synthetic

<400> SEQUENCE: 28 ctactttttcc cacattggcc tgagagctgt agtacaaaaa acaccgcgcg gtctggagct     60
ctccataagc ccgcagaaca aaagctgcga tttgcccaaa aaccttgcca tggcaactat    120
acagtcaccc cttgcgggtt attgcattgg attcaatctc caggcagtt gtagccccct     180 tttatgatat gcgaggatac ttaacgtgtc tgaatgtgga atataatgtg aaaggaaagc    240
agcgcccact ggtgtatcag aacagtggtg cactacctat ctgctcattc gttgtttcgg    300
ttctgtgttt tccgtc                                                    316

<210> SEQ ID NO 29
<211> LENGTH: 303
<212> TYPE: DNA
<213> ORGANISM: Artificial Sequence
<220> FEATURE:
<223> OTHER INFORMATION: Synthetic

<400> SEQUENCE: 29 ctactttttcc cacattggcc tgagagctgt agtacaaaaa acaccgcgcg gtctggagct     60
ctccataagc ccgcagaaca aaagctgcga tttgcccaaa aaccttgcca tggcaactat    120
acagtcaccc cttgcgggtt attgcattgg attcaatctc caggcagtt gtagccccct     180 tttatgatat gcgaggatac ttaacgtgtc tgaatgtgga atataatgtg aaaggaaagc    240
agcgcccact ggtgtatcag aacagtggtg cactacctat ctgctcattc gttgtttccc    300
gtc                                                                  303

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
caaagctacg aggaggcagg                                                 20

<210> SEQ ID NO 31
<211> LENGTH: 22
<212> TYPE: DNA
<213> ORGANISM: Artificial Sequence
<220> FEATURE:
<223> OTHER INFORMATION: Synthetic

<400> SEQUENCE: 31
cgccgacacc aacgcatcaa ac                                              22
```

```
<210> SEQ ID NO 32
<211> LENGTH: 22
<212> TYPE: DNA
<213> ORGANISM: Artificial Sequence
<220> FEATURE:
<223> OTHER INFORMATION: Synthetic

<400> SEQUENCE: 32
ggcgatataa cgactgaaca ga                                              22

<210> SEQ ID NO 33
<211> LENGTH: 19
<212> TYPE: DNA
<213> ORGANISM: Artificial Sequence
<220> FEATURE:
<223> OTHER INFORMATION: Synthetic

<400> SEQUENCE: 33
cgcccactgg tgtatcaga                                                  19

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
aatcgcagct tttgttctgc                                                 20

<210> SEQ ID NO 35
<211> LENGTH: 17
<212> TYPE: DNA
<213> ORGANISM: Artificial Sequence
<220> FEATURE:
<223> OTHER INFORMATION: Synthetic

<400> SEQUENCE: 35
cgcttgcctg gtcctgg                                                    17

<210> SEQ ID NO 36
<211> LENGTH: 17
<212> TYPE: DNA
<213> ORGANISM: Artificial Sequence
<220> FEATURE:
<223> OTHER INFORMATION: Synthetic

<400> SEQUENCE: 36
caggcgtacc gggccag                                                    17

<210> SEQ ID NO 37
<211> LENGTH: 17
<212> TYPE: DNA
<213> ORGANISM: Artificial Sequence
<220> FEATURE:
<223> OTHER INFORMATION: Synthetic

<400> SEQUENCE: 37
caccagcgat tagcgcg                                                    17

<210> SEQ ID NO 38
<211> LENGTH: 22
<212> TYPE: DNA
<213> ORGANISM: Artificial Sequence
```

```
<220> FEATURE:
<223> OTHER INFORMATION: Synthetic

<400> SEQUENCE: 38
ggtcattaga tgctgccgct ac                                              22

<210> SEQ ID NO 39
<211> LENGTH: 19
<212> TYPE: DNA
<213> ORGANISM: Artificial Sequence
<220> FEATURE:
<223> OTHER INFORMATION: Synthetic

<400> SEQUENCE: 39
gcagcggcat atgagctgg                                                  19

<210> SEQ ID NO 40
<211> LENGTH: 22
<212> TYPE: DNA
<213> ORGANISM: Artificial Sequence
<220> FEATURE:
<223> OTHER INFORMATION: Synthetic

<400> SEQUENCE: 40
ggtcattaga tgctgccgct ac                                              22

<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41
catttgatga ggagtgtgat agag                                            24

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
ttctgtgttt gtctgattct tag                                             23

<210> SEQ ID NO 43
<211> LENGTH: 19
<212> TYPE: DNA
<213> ORGANISM: Artificial Sequence
<220> FEATURE:
<223> OTHER INFORMATION: Sythentic

<400> SEQUENCE: 43
ccgaaacaac gaatgagca                                                  19

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
ggtcaagtag ctgcgtccaa a                                               21
```

```
<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
gtcatcaatg gaaatcccat cacc                                           24

<210> SEQ ID NO 46
<211> LENGTH: 22
<212> TYPE: DNA
<213> ORGANISM: Artificial Sequence
<220> FEATURE:
<223> OTHER INFORMATION: Synthetic

<400> SEQUENCE: 46
tgagtccttc cacgatacca aa                                             22

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
tgcaccacca actgcttagc                                                20

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
ggcatggact gtggtcatga g                                              21

<210> SEQ ID NO 49
<211> LENGTH: 22
<212> TYPE: DNA
<213> ORGANISM: Artificial Sequence
<220> FEATURE:
<223> OTHER INFORMATION: Synthentic

<400> SEQUENCE: 49
cacactgtgc ccatctatga gg                                             22

<210> SEQ ID NO 50
<211> LENGTH: 22
<212> TYPE: DNA
<213> ORGANISM: Artificial Sequence
<220> FEATURE:
<223> OTHER INFORMATION: Synthetic

<400> SEQUENCE: 50
tcgaagtcta gggcgacata gc                                             22

<210> SEQ ID NO 51
<211> LENGTH: 22
<212> TYPE: DNA
<213> ORGANISM: Artificial Sequence
```

<220> FEATURE:
<223> OTHER INFORMATION: Synthetic

<400> SEQUENCE: 51
cgaacgtctg ccctatcaac tt                                              22

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
tgtggtagcc gtttctcagg                                                 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
ttcaaaacac gcaccgcttg                                                 20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
aaacgtggac gtcatggagc                                                 20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
cgcctgtaga acggaaacat                                                 20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
ttgcccgcct ctattatcag                                                 20

<210> SEQ ID NO 57
<211> LENGTH: 22
<212> TYPE: DNA
<213> ORGANISM: Artificial Sequence
<220> FEATURE:
<223> OTHER INFORMATION: Synthetic

<400> SEQUENCE: 57
tttagtgtag agggaccttg gg                                              22

```
<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
tctccatctc ctgcattgcc                                          20

<210> SEQ ID NO 59
<211> LENGTH: 22
<212> TYPE: DNA
<213> ORGANISM: Artificial Sequence
<220> FEATURE:
<223> OTHER INFORMATION: Synthetic

<400> SEQUENCE: 59
cagagtctat tcgccctgtt ag                                       22

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
ctggtacagt ccttgcagaa ta                                       22

<210> SEQ ID NO 61
<211> LENGTH: 23
<212> TYPE: DNA
<213> ORGANISM: Artificial Sequence
<220> FEATURE:
<223> OTHER INFORMATION: Synthetic

<400> SEQUENCE: 61
ccaagaggcg actacataga aag                                      23

<210> SEQ ID NO 62
<211> LENGTH: 22
<212> TYPE: DNA
<213> ORGANISM: Artificial Sequence
<220> FEATURE:
<223> OTHER INFORMATION: Synthetic

<400> SEQUENCE: 62
gggtgatgtt ccctaccttA ac                                       22

<210> SEQ ID NO 63
<211> LENGTH: 21
<212> TYPE: DNA
<213> ORGANISM: Artificial Sequence
<220> FEATURE:
<223> OTHER INFORMATION: Synthetic

<400> SEQUENCE: 63
tgggcgagtt tattggtagt g                                        21

<210> SEQ ID NO 64
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 64
cgctgatgtg cgttcatttg                                                    20

<210> SEQ ID NO 65
<211> LENGTH: 23
<212> TYPE: DNA
<213> ORGANISM: Artificial Sequence
<220> FEATURE:
<223> OTHER INFORMATION: Synthetic

<400> SEQUENCE: 65
caggcagcag tagaatcaga taa                                                23

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
gacggtcgtg tggtacataa a                                                  21

<210> SEQ ID NO 67
<211> LENGTH: 21
<212> TYPE: DNA
<213> ORGANISM: Artificial Sequence
<220> FEATURE:
<223> OTHER INFORMATION: Synthetic

<400> SEQUENCE: 67
tgcctgcctg taattgttgc g                                                  21

<210> SEQ ID NO 68
<211> LENGTH: 19
<212> TYPE: DNA
<213> ORGANISM: Artificial Sequence
<220> FEATURE:
<223> OTHER INFORMATION: Synthetic

<400> SEQUENCE: 68
gcagcggcat atgagctgg                                                     19

<210> SEQ ID NO 69
<211> LENGTH: 283
<212> TYPE: DNA
<213> ORGANISM: Artificial Sequence
<220> FEATURE:
<223> OTHER INFORMATION: Synthetic

<400> SEQUENCE: 69
gtttgtgtct gtgctgcaga agctcatggg cctaacggcc tgcctgcgcc gcatgcgtca        60
caagatcaaa gagattgggg ccccgctttt tgacagcgta atccccggct tccggtctgc       120
aacctggtcc tggacctgga tctaaagatc aaggggcccc cctggtcgct ggaggaaatc       180
tatgacctgt gccggaccgt gcggcgtgag gtactgcgcc tcatgcgccg cctgggtcca       240
gtgtccaggg cccacccagt ctatttttc aaatcagctt gtc                         283
```

<210> SEQ ID NO 70
<211> LENGTH: 274
<212> TYPE: DNA
<213> ORGANISM: Artificial Sequence
<220> FEATURE:
<223> OTHER INFORMATION: Synthetic

<400> SEQUENCE: 70
gtcactcacg tcctcctcct ggatagactg ggaggcctga acccccagag tgtagctgct      60
gctctgtgaa gtctcttcct cctcgtccga caagaggcgc cggtccctgc aagaccggac     120
cccacgcgac ttcagaaaca tggccatagt gatgacccct ctacagcctc caaagtcaga     180
ctcgtctgaa tctgaaggat gccacgaggg gtcgctatca ctgccctcag atgggtcttc     240
gtcactgggg tactcttcct ccaaatcaat ctcc                                  274

<210> SEQ ID NO 71
<211> LENGTH: 208
<212> TYPE: DNA
<213> ORGANISM: Artificial Sequence
<220> FEATURE:
<223> OTHER INFORMATION: Synthetic

<400> SEQUENCE: 71
ggcgggtagt tattggctcc gagattctag aaacacgtgt cccgctgacg caggggcct      60 tgcttcccct gttattctga tagaatgaca gcctgtaaca caaagtggaa gcagcactta    120
tcagcgttgg aggcacgggg gcaaaggtca agtagctgcg tccaaattca gctcagtgac    180
acgtccaacg gcatatcacg tgtatgtg                                        208

<210> SEQ ID NO 72
<211> LENGTH: 150
<212> TYPE: DNA
<213> ORGANISM: Artificial Sequence
<220> FEATURE:
<223> OTHER INFORMATION: Synthetic

<400> SEQUENCE: 72
gccggacctg taacacaaag tggaagcagc acttatcagc gttggaggca cggggggcaaa     60 ggtcaagtag ctgcgtccaa attcagctca gtgacacgtc caacggcatc ttgcccgtcg    120
acgagctccg gccatggccg aagcttaccc                                      150

<210> SEQ ID NO 73
<211> LENGTH: 262
<212> TYPE: DNA
<213> ORGANISM: Artificial Sequence
<220> FEATURE:
<223> OTHER INFORMATION: Synthetic

<400> SEQUENCE: 73
gcactctgac caggacatcg tgctaagcgt cctgaatccg cgcagcctgc tggcgcagca      60
cacgccccca tttctaaagt catacgcccg tattcacaca ttcccgggga aggtgtgtcc    120
ggtcaacgcc atacgccgcg gtaagggcta cgtccgagtc tccgtggaca cgccggacct    180
tgcccgtcga cgagctccgg ccatggccga agcttacccc ggaggagccc atgcagcact    240
agcgtcccgg cgctcgtcgt tc                                              262

<210> SEQ ID NO 74
<211> LENGTH: 260
<212> TYPE: DNA
<213> ORGANISM: Artificial Sequence -continued

```
<220> FEATURE:
<223> OTHER INFORMATION: Synthetic

<400> SEQUENCE: 74
ggtttgttta gcagcctggt ctcgggtttc atctccttct tcaaaaaccc cttcggcggc      60
atgctcattc tggtcctggt ggcgcctacc gccacgcgtc agcaaaccag ctttcctttc     120
cgagtctgcg agctctccag ccacggcgac ctgttccgct tctcctcgga catccagtgt     180
ccctcgtttg gcacgcggga gaatcacacg gagggcggga cgaacagcgt gcctccaacg     240
tctttgacct ggagggcatc                                                  260

<210> SEQ ID NO 75
<211> LENGTH: 291
<212> TYPE: DNA
<213> ORGANISM: Artificial Sequence
<220> FEATURE:
<223> OTHER INFORMATION: Synthetic

<400> SEQUENCE: 75
gcattgtgga acacgtagat gtccctgtga taggaggtag cgcgtaggag cccgcagttg      60
gggtcgggcc tcctgtgcag agccttgaca tggttgactt cgagacccccc gagacgtaga   120 ggacggaatt ggtggcaaag atctgcgtgg ccaccttggc ctggtcctgc aggctctgct    180
tctccagcag ctccaccagc ttgcccaccc gtcggacgcg cagcgcctgc gccagcccgg    240
tgtacagcgc ctcgtgcatg cagcggctga ggtccgagtt gtaaaactgg c              291

<210> SEQ ID NO 76
<211> LENGTH: 270
<212> TYPE: DNA
<213> ORGANISM: Artificial Sequence
<220> FEATURE:
<223> OTHER INFORMATION: Synthetic

<400> SEQUENCE: 76
agtccacttg gagccctttg tctactccta ctgatgagta agtattacac cctttgcccc      60 acacccctt tcccttactc ttccttctct aacgcacttt ctcctctttc cccagtcacc     120
ctcctgctca tcgcactctg gatttttcga catggacaac gacacagtga tgaacaccac    180
cacgatgact ccctcccgca ccctcaacaa gctaccgatg attctagcca tgaaattccc    240
atctccgccg tctgctgctt cgtcacccgc                                      270
```

GAMMA HERPESVIRUS CIRCULAR RNA

CROSS-REFERENCE TO RELATED APPLICATIONS

This patent application is the U.S. national phase of PCT/2019/034995, filed May 31, 2019, which claims the benefit of U.S. Provisional Patent Application Nos. 62/679,698; 62/679,712; and 62/679,725, each of which was filed on Jun. 1, 2018, wherein each application is incorporated herein by reference in its entirety herein.

STATEMENT REGARDING FEDERALLY SPONSORED RESEARCH OR DEVELOPMENT

This invention was made with Government support under Grant Number CA197463 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 24,467 Byte ASCII (Text) filed named 750957_ST25.txt dated Nov. 24, 2020.

BACKGROUND OF THE INVENTION

Circular RNAs (circRNA) originate from exonic backsplicing into an exon acceptor sequence, generating a highly stable, circular RNA. circRNAs may generate non-canonical protein, act as a scaffold for protein-protein interactions, modulate transcription and serve as RNA-binding protein or miRNA sponges and can be readily detected in fixed tissues. As of the priority date of the present patent application, it is believed that no circRNAs from DNA tumor viruses have been described, although certain plant viroids and hepatitis D virus are examples of circular single stranded RNA viruses.

EBV and KSHV are two prevalent members of the taxonomic group "Gammaherpesvirinae," or γ-herpesviruses. This taxa includes several human, but also non-human, viruses, generally classified into four genera: *Percavirus, Macavirus, Lymphocryptovirus,* and *Rhadinovirus*. Exemplary γ-herpesviruses are described in Escalera-Zamudio et al. 7(6):e01425-16. doi:10.1128/mBio.01425-16 (incorporated herein by reference), especially supplemental table S5. Exemplary γ-herpesviruses include, but are not limited to Alcelaphine herpesvirus 1, *Apodemus sylvaticus* rhadinovirus 1, Ateline herpesvirus 3, *Babyrousa babyrussa* rhadinovirus 1, *Bandicota indica* rhadinovirus 4, *Bandicota savilei* rhadinovirus 1, Bovine herpesvirus 4, Bovine herpesvirus 6, Bovine lymphotropic herpesvirus, Callitrichine herpesvirus 3, Caprine herpesvirus 2, Cercopithicine herpesvirus 15, *Crocuta crocuta* gammaherpesvirus 1, *Cynopterus sphinx* 13HN70, *Cynopterus sphinx* CS/12GZ1, *Cynopterus sphinx* CS/14GZ24, *Diceros bicornis* gammaherpesvirus, *Diceros bicornis* gammaherpesvirus 1, *Elephas maximus* gammaherpesvirus 1, *Eptesicus serotinus* rhadinovirus 1, Equid herpesvirus 2, Equid herpesvirus 5, *Equus zebra* gammaherpesvirus 1, *Equus zebra* gammaherpesvirus 1, *Felis catus* gammaherpesvirus 1, *Gorilla gorilla* lymphocryptovirus 1, Gorilla rhadinovirus 1, *Hexaprotodon liberiensis* gammaherpesvirus 1, *Hipposideros diadema* herpesvirus, *Hipposideros larvatus* HL/11HN1, *Hipposideros pomona* 211HN104, *Hipposideros pomona* HP/11HN104, *Hipposideros pomona* HP/11HN110, Human herpesvirus 4, Human herpesvirus 8, Lymphocryptovirus Macaca, *Lynx rufus* gammaherpesvirus 1, *Macaca fascicularis* lymphocryptovirus 1, *Macaca fascicularis* rhadinovirus 2, *Macaca fuscata* rhadinovirus, *Miniopterus schreibersii* 11HN110, *Miniopterus schreibersii* 211HN16, *Miniopterus schreibersii* MS/11HN95, *Miniopterus schreibersii* MS/12HN28, Murid herpesvirus 4, *Mus cervicolor* rhadinovirus 1, *Mus musculus* rhadinovirus 1, Mustelid herpesvirus 1, *Myodes glareolus* rhadinovirus 1, *Myotis nattereri* rhadinovirus 1, *Myotis ricketti* herpesvirus 1, *Myotis ricketti* herpesvirus 2, *Myotis velifer* gammaherpesvirus 8, *Nyctalus noctula* rhadinovirus 1, *Nyctalus noctula* rhadinovirus 2, Ovine herpesvirus 2, *Pan troglodytes* rhadinovirus 2, *Pan troglodytes* rhadinovirus 3, *Panthera leo* gammaherpesvirus 1, *Papio hamadryas* lymphocryptovirus 2, *Pipistrellus nathusii* rhadinovirus 1, *Pipistrellus pipistrellus* rhadinovirus 1, *Plecotus auritus* rhadinovirus 1, Porcine lymphotropic herpesvirus 2, Porcine lymphotropic herpesvirus 2, Porcine lymphotropic herpesvirus 3, *Procavia capensis* gammaherpesvirus 2, *Ptenochirus jagori* gammaherpesvirus, *Pteropus giganteus* herpesvirus 2, *Pteropus giganteus* herpesvirus 3, *Pteropus giganteus* herpesvirus 5, *Pteropus giganteus* herpesvirus 6, *Puma concolor* gammaherpesvirus 1, *Rhinolophus blythi* 13HN56, *Rhinolophus blythi* 13YF104, *Rhinolophus blythi* 13YF79, *Rhinolophus blythi* 13YF82, *Rhinolophus blythi* 13YF84, *Rhinolophus blythi* 13YF87, *Rhinolophus blythi* 13YF96, *Rhinolophus blythi* RB/13YF11, *Rhinolophus blythi* RB/13YF3, *Rhinolophus blythi* RB/13YF6, *Rhinolophus blythi* RB/13YF84, *Rhinolophus blythi* RB/13YF87, *Rhinolophus blythi* RB/13YF89, *Rhinolophus blythi* RB/13YF96, *Rhinolophus blythi* RB/13YF99, *Rupicapra rupicapra* gammaherpesvirus 1, *Saimiri sciureus* gammaherpesvirus 2, Saimiriine herpesvirus 2, *Scotophilus kuhlii* 11HZ76, *Scotophilus kuhlii* 13Y234, *Scotophilus kuhlii* 13YF106, *Scotophilus kuhlii* 13YF114, *Scotophilus kuhlii* 13YF15, *Scotophilus kuhlii* 13YF155, *Scotophilus kuhlii* 13YF160, *Scotophilus kuhlii* 13YF187, *Scotophilus kuhlii* 13YF206, *Scotophilus kuhlii* 13YF244, *Scotophilus kuhlii* SK/11HZ84, *Scotophilus kuhlii* SK/13YF121, *Scotophilus kuhlii* SK/13YF14, *Scotophilus kuhlii* SK/13YF146, *Scotophilus kuhlii* SK/13YF15, *Scotophilus kuhlii* SK/13YF16, *Scotophilus kuhlii* SK/13YF185, *Scotophilus kuhlii* SK/13YF239, *Sorex araneus* gammaherpesvirus 1, *Sus barbatus* rhadinovirus 1, *Symphalangus syndactylus* lymphocryptovirus 2, *Tapirus terrestris* gammaherpesvirus 1, *Tupaia belangeri* gammaherpesvirus 1, and Type 2 ruminant rhadinovirus of mule deer. γ-Herpesviruses are trophic for, and replicate within, lymphoid cells, but they are capable of undergoing lytic infection/replication in epithelial cells and fibroblasts.

Epstein-Barr Virus is one such DNA tumor virus. It is estimated that a large majority (perhaps 90% to 95%) of humans are infected with EBV. Although primary infection with EBV during early childhood is asymptomatic, delayed onsets can be associated with infectious mononucleosis, which rarely leads to severe complications. However, such individuals can pass EBV infection to another person, such as a person not infected with EBV. In a minority of EBV-infected people, however, the EBV infection becomes lytic, resulting in a much higher copy number of EBV viruses either in circulation or in a tumor. These individuals may develop certain cancers, such as lymphomas and nasopharyngeal cancer. As such, there remains a need for methods and reagents for identifying people experiencing lytic EBV infection or at risk of such.

Kaposi's Sarcoma-Associated Herpesvirus (KSHV) is also one such DNA tumor virus. The virus can cause Kaposi's sarcoma, a type of cancer not uncommon in HIV-infected individuals, organ transplant recipients, or other immunocompromised individuals, and older or elderly adults. KSHV also can cause certain types of lymphomas and other disorders. In the northern European and north American population, KSHV is a relatively rare infection (perhaps about 3% of the population being infected), but KSHV infection is more prevalent in African and Mediterranean countries. While blood tests assaying for the presence of anti-KSHV antibodies exist, there remains a need for methods and reagents for identifying people experiencing KSHV infection.

While blood tests assaying for the presence of some γ-herpesviruses exist, there remains a need for methods and reagents for identifying mammals infected with γ-herpesviruses.

BRIEF SUMMARY OF THE INVENTION

In an embodiment, the invention provides a method and reagents for detection of γ-herpesvirus circRNA. In an embodiment, the invention provides a method and reagents for detection of EBV circRNA. In an embodiment, the invention provides a method and reagents for detection of KSHV circRNA. Also, the method can be expanded to other herpesviruses and even non-herpesviruses that generate circRNA upon cellular infection.

DESCRIPTION OF THE SEVERAL VIEWS OF THE DRAWINGS

FIG. 2A shows an example of an EBV circRNA sequence (circBART-akata 711nuc) identified in the sequencing analysis of the Akata strain in Example 1.

FIG. 2B shows an EBV circRNA map (circBART Akata4) derived from the results of the sequencing analysis of the Akata strain in Example 1.

FIG. 3A shows an example of an EBV circRNA sequence (circRPMS1-akata 609nuc) identified in the sequencing analysis of the Akata strain in Example 1.

FIG. 3B shows an EBV circRNA map (circBART Akata3) derived from the results of the sequencing analysis of the Akata strain in Example 1.

FIG. 4A shows an example of an EBV circRNA sequence (circRPMS1-akata 501nuc) identified in the sequencing analysis of the Akata strain in Example 1.

FIG. 4B shows an EBV circRNA map (circBART Akata2) derived from the results of the sequencing analysis of the Akata strain in Example 1.

FIG. 5A shows an example of an EBV circRNA sequence (circRPMS1-akata 399nuc) identified in the sequencing analysis of the Akata strain in Example 1.

FIG. 5B shows an EBV circRNA map (circBART Akata1) derived from the results of the sequencing analysis of the Akata strain in Example 1.

FIG. 6A shows an example of a KSHV circRNA (KSHV circ-vIRF4) identified in the sequencing analysis in Example 2. The sequence is conserved among cell lines such as BC1, BCBL1 and BCP1.

FIG. 6B shows a KSHV circRNA map (circKSHV-vIRF4) derived from the results of the sequencing analysis of Example 2.

FIG. 7A shows an example of a KSHV circRNA sequence (circPAN(-) 28692-29016) identified in the sequencing analysis in Example 2.

FIG. 7B shows an example of a KSHV circRNA sequence (circPAN(-) 28519-29016) identified in the sequencing analysis in Example 2.

FIG. 7C shows an example of a KSHV circRNA sequence (circPAN(-) 28420-28717) identified in the sequencing analysis in Example 2.

FIG. 7D shows an example of a KSHV circRNA sequence (circPAN(-) 28290-28691) identified in the sequencing analysis in Example 2.

FIG. 7E shows an example of a KSHV circRNA sequence (circPAN(-) 28290-28593) identified in the sequencing analysis in Example 2.

FIG. 7F shows an example of a KSHV circRNA sequence (circPAN(-) 28406-29099) identified in the sequencing analysis in Example 2.

FIG. 7G shows an example of a KSHV circRNA sequence (circPAN(-) 28406-28888) identified in the sequencing analysis in Example 2.

FIG. 7H shws an example of a KSHV circRNA sequence (circPAN(-) 28406-28721) identified in the sequencing analysis in Example 2.

FIG. 7I shows an example of a KSHV circRNA sequence (circPAN(-) 28406-28708) identified in the sequencing analysis in Example 2.

DETAILED DESCRIPTION OF THE INVENTION

Figure 1:
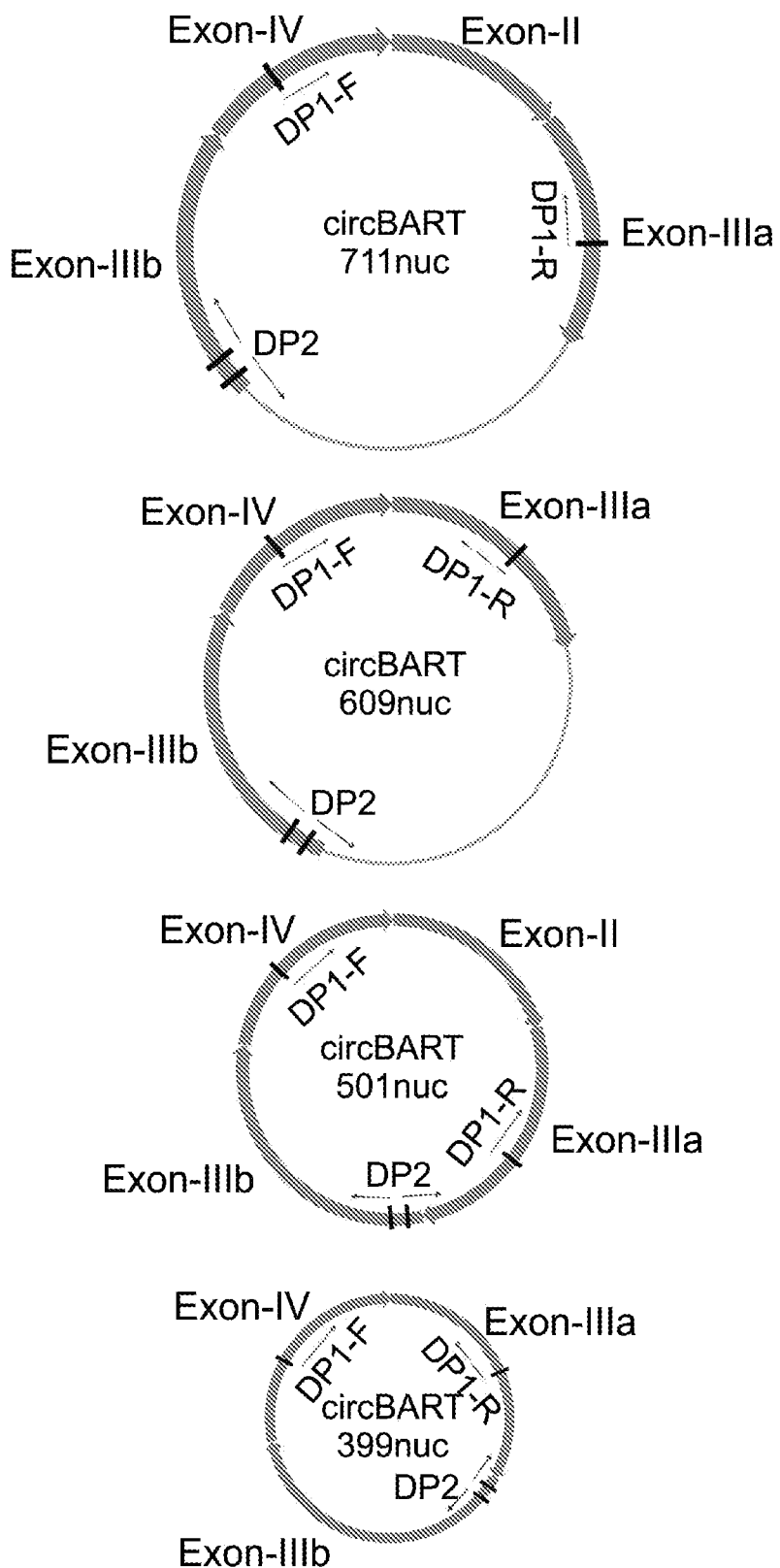
FIG. 1 depicts the relationships between primers DP1-R (reverse): CGCCCGTATTCACACATTCC (SEQ ID NO:1), and DP1-F (forward): GACGCTAGTGCTGCATGGG (SEQ ID NO:2), DP2-F (forward): and TGAGGAATACCTCGTTGTCTTCCG (SEQ ID NO:3) and DP2-R (reverse): AGCCCTTCTTCGTTATGCAC (SEQ ID NO:4) vis-à-vis circBART (EBV) circRNA.

The invention provides a method and reagents for detection of γ-herpesvirus circRNA. In accordance with one aspect of the method, a tissue or fluid sample is obtained, RNA is extracted from the tissue sample, and then the RNA is assayed to determine the presence of γ-herpesvirus circRNA. In another aspect of the method, the sample is assayed to determine the presence of γ-herpesvirus circRNA in situ, which need not require extraction of RNA from the sample.

In accordance with the inventive method, for detection of γ-herpesvirus, the tissue sample can be any tissue or fluid, but typically will be tissue or fluid suspected of possessing high levels of γ-herpesvirus associated with lytic infection. Fluid samples that can be tested include saliva, whole blood or products thereof (e.g., plasma), urine, sweat, lymphatic fluid, cerebro-spinal fluid, or other desired fluid. For example, in connection with one exemplary γ-herpesvirus (EBV), the tissue or fluid sample can include those suspected EBV-related tumors (e.g., nasopharyngeal tissues, including tumors thereof), blood or products thereof (e.g., plasma, packed red cells, etc.), bone marrow, lymph node biopsies, etc. For a second exemplary γ-herpesvirus (KSHV), the tissue or fluid sample can include suspected KSHV-related tumors (e.g., skin, lymphatic tissue, etc.), blood or products thereof (e.g., plasma, packed red cells, etc.), bone marrow, lymph node biopsies, etc. Also, tissue samples suitable for use in the inventive method can include, for example, such tissues not necessarily suspected of γ-herpesvirus infection, in which the inventive method can be used to help assess the risk of the emergence of γ-herpesvirus-related clinical symptoms in an individual subject or a population or the study of archived tissue samples. Also, biopsies from transplanted organs or other tissue (in which the inventive method can be employed to monitor the outcome of the transplant procedure, for example), can be employed. These fluid and tissue samples are merely exemplary, and a skilled artisan or treating physician can select any desired fluid or tissue samples for assay according to the inventive method.

The source of the tissue typically will be human, either a human patient, a human cadaver, or fixed and preserved human tissue. However, the method is applicable to non-human animals as well, particularly mammals (but avian species may also be assayed). For example, the method may be employed with tissue or fluid samples from commonly-used laboratory animals (e.g., mice, rats, etc.), companion animals (cats, dogs, etc.), in veterinary use with large and small mammals (e.g., swine, horses, cows, goats, sheep, etc.), or with tissue or fluid samples from other animals of zoological importance (e.g., rare or endangered animals, dolphins, elephants, large cats, ungulates, non-human primates (such as old world and new world monkeys: baboon, gorilla, chimpanzee, rhesus, marmosets), etc.). In particular, γ-herpesviruses are known to be species-specific for non-human animals, such as Rhesus monkeys (for example, Rhesus monkey rhadinovirus (VRR)), horses (for example, Equine herpesvirus 2), mice (for example, Murid herpesvirus 68), elephants (for example, Elephantid herpesvirus 3, Elephantid herpesvirus 4, Elephantid herpesvirus 5), dolphins (for example, Common bottlenose dolphin gammaherpesvirus 1), and other taxonomic groups (exemplary γ-herpesviruses include cynomys herpesvirus 1 (CynGHV-1), Procavid herpesvirus 1, and Trichechid herpesvirus 1). Thus, these known hosts of γ-herpesviruses are of particular relevance as sources for fluid or tissue samples for use in accordance with the inventive method, though they are not exclusive but rather exemplary.

For example, the method may be performed on non-human cells, fluid, or tissue samples drawn from species suspected of being infected with EBV, which may be of particular importance in the laboratory context in which non-human animals (e.g., mice, rats, or non-human primates (such as old world and new world monkeys: baboon, gorilla, chimpanzee, rhesus, marmosets)) may be exposed to EBV, such as for ethical experimental purposes. Other tissue samples that can be tested include suspected KSHV-related tumors (e.g., skin, lymphatic tissue, etc.), blood or products thereof (e.g., plasma, packed red cells, etc.), bone marrow, lymph node biopsies, etc.

In accordance with the inventive method, the fluid or tissue sample is processed according to standard methods and then exposed to reagents and processes that can detect the presence of γ-herpesvirus circRNA. For example, RNA can be extracted from the sample and then purified prior to the assay to detect the presence of γ-herpesvirus circRNA. Alternatively, tissue can be fixed and preserved (e.g., in paraffin) to permit in situ detection of the γ-herpesvirus circRNA. Generally, it may be preferred to treat either the extracted γ-herpesvirus or fixed and preserved tissue with RNAse R prior to the assay for detection of the γ-herpesvirus circRNA. This is because RNAse R degrades linear RNAs but does not degrade circRNAs. Eliminating or reducing the presence of linear RNAs by treating the extracted RNA or fixed and preserved tissue with RNAse R prior to the assay for the presence of γ-herpesvirus circRNA, thus, can reduce "noise" attributable to the presence of linear RNA, increasing the fidelity of the detection of circRNA specifically.

Typically, such methods include reverse transcription PCR (rtPCR) employing a set of primers that specifically hybridize to the γ-herpesvirus circRNA. The rtPCR can be conducted using standard methodology using the extracted RNA or fixed and preserved tissue as a template source for RNA. When rtPCR is employed, preferably hot-start and high-fidelity polymerases are used to minimize the likelihood of PCR-related mutations attributable to the amplification step. Also, divergent primers flanking the junction site are designed and used for this purpose so that the PCR step will only produce a product if the template is circular, thus the linear templates will not give any amplified product. However, the inventive method is not limited to the use of rtPCR but can employ other methods able to detect the presence of γ-herpesvirus circRNA. For example, Northern Blots or FISH can be employed (see, e.g., (DOI: 10.1007/978-1-4939-7562-4_10 and DOI: 10.1007/978-1-4939-7562-4_7, each of which is incorporated herein by reference).

As noted herein, EBV is one example of a human γ-herpesvirus of relevance to the inventive method. An example of a pair of divergent primers suitable for detection of EBV circRNA via rtPCR is DP1: DP1-R (reverse): CGCCCGT-ATTCACACATTCC (SEQ ID NO:1) and DP1-F (forward): GACGCTAGTGCTGCATGGG (SEQ ID NO:2). Divergent primer (DP)1 primer pair flanks the backsplice junction site between Exon-IV and Exon IIIa for cRPMS1 609 and 339 and the PCR product is 162 bp (cRPMS1 SJ). Between ExonIV and ExonII for cRPMS1 711 and 501, the PCR product is 264 bp (cRPMS1 LJ). Another example of a pair of divergent primers suitable for detection of EBV circRNA via rtPCR is DP2: DP2-F (forward): TGAG-GAATACCTCGTTGTCTTCCG (SEQ ID NO:3) and DP2-R (reverse): AGCCCTTCTTCGTTATGCAC (SEQ ID NO:4). Using these primers (DP2), four different rtPCR circBART products (711 bp, 609 bp, 501 bp, and 339 bp) can be obtained. Schematics of these primers in relation to circBART are presented in FIG. 1. However, the method is not limited to the use of these specific primer pairs (DP1 (SEQ ID Nos: 1 and 2) and DP2 (SEQ ID Nos: 3 and 4)) but can use other primers that a person of ordinary skill in the art might design to identify the EBV circRNA.

For EBV, the method can be employed in a diagnostic context to identify, or (if no EBV circRNA is detected) rule-out lytic EBV infection as associated with a given condition. The method also can be used to screen an individual or population to assess risk of a condition associated with lytic EBV infection, such as nasopharyngeal carcinoma or infectious mononucleosis, for example. In this aspect, the positive identification of EBV circRNA can indicate a heightened risk for contracting such a condition. The method also can be employed in monitoring organ or tissue transplant recipients, e.g., the presence of EBV circRNA either in the transplanted organ or tissue, or in other tissues of the transplant recipient may permit early treatment or prophylaxis for EBV-related diseases in the organ or tissue recipient.

As noted herein, KSHV is another example of a human γ-herpesvirus of relevance to the inventive method. An example of a pair of primers suitable for detection of KSHV circRNA via rtPCR is: circvIRF4 R (reverse): CAAATG-CATGGTACACCGAATAC (SEQ ID NO:5) and circvIRF4 F (forward): GAACCGCTATTACAATGTTGGC (SEQ ID NO:6). Using these primers, an rtPCR product is expected to be 158 nucleotides/basepairs. However, the method is not limited to the use of this specific primer pair (SEQ ID Nos: 5 and 6) but can use other primers that a person of ordinary skill in the art might design to identify the KSHV circRNA.

For KSHV, the method can be employed in a diagnostic context to identify, or (if no KSHV circRNA is detected) rule-out KSHV infection as associated with a given condition. The method also can be used to screen an individual or population to assess risk of a condition associated with lytic KSHV infection, such as Karposi's Sarcoma, primary effusion lymphoma and multicentric Castleman's disease and KSHV inflammatory cytokine syndrome. In this aspect, the positive identification of KSHV circRNA can indicate a heightened risk for contracting such a condition. The method also can be employed in monitoring organ or tissue transplant recipients, e.g., the presence of KSHV circRNA either in the transplanted organ or tissue, or in other tissues of the transplant recipient may permit early treatment or prophylaxis for KSHV-related diseases in the organ or tissue recipient.

The method can be extended beyond γ-herpesviruses to include other herpesviruses, or indeed any double-stranded DNA virus that generates circRNA from its genome upon infection of a cell, especially a mammalian cell. Accordingly, the invention provides a method comprising obtaining a tissue or fluid sample from a subject (preferably a mammalian subject) and assaying the tissue or fluid sample to determine the presence of viral circRNA. As noted here, in performance of the method, RNA can be extracted from the tissue sample, and then the extracted RNA is assayed to determine the presence of circRNA. Alternatively, the method can be used directly on such tissue or fluid sample (e.g., in situ). However, the method desirably should be able to distinguish between viral circRNA and linear viral RNA, as through the use of RNA R. Also, while, as noted, other methods can be used, desirably, the method involves divergent reverse transcription PCR (rtPCR).

The invention also provides, as reagents for detecting the presence of γ-herpesvirus circRNA, a composition comprising one or more primers able to hybridize to γ-herpesvirus circRNA in an rtPCR assay. Such primers typically are DNA molecules, and they typically comprise between about 10 and about 30 nucleotides (such as 10, 11, 12, 13, 14, 15, 16, 17, 18, 19, 20, 21, 22, 23, 24, 25, 26, 27, 28, 29, or, 30 nucleotides), more preferably between 18 and 27 nucleotides. As noted above, exemplary primers for EBV include DP1-R: CGCCCGTATTCACACATTCC (SEQ ID NO:1), DP1-F: GACGCTAGTGCTGCATGGG (SEQ ID NO:2), DP2-F: TGAGGAATACCTCGTTGTCTTCCG (SEQ ID NO:3) and DP2-R: AGCCCTTCTTCGTTATGCAC (SEQ ID NO:4). Exemplary primers for detection of KSHV circRNA via rtPCR include circvIRF4 R: CAAATGCATGGTACACCGAATAC (SEQ ID NO:5) and circvIRF4 F: GAACCGCTATTACAATGTTGGC (SEQ ID NO:6). Designing primers for rtPCR is within the scope of knowledge and skill for a person of ordinary skill in the art; therefore, other primers than these exemplary ones can be designed to hybridize to γ-herpesvirus circRNA. However, for use in the detection of circRNA, the primers should be divergent primers and flank the backsplice site. Also, primers for use in rtPCR desirably have a Tm between 57-63° C.; also, self-dimerization and strong hairpin formation also desirably should be avoided. To this end, relevant template sequences are presented below in the Examples entitled "EXAMPLE 1-Epstein-Barr Virus (EBV) circRNA" and "EXAMPLE 2-Kaposi's Sarcoma-Associated Herpesvirus (KSHV) circRNA." The primers can be formulated in any suitable preparation, such as in lyophilized form (possibly including a lyoprotectant), or in solution, such as including buffers and preservatives, if desired.

The invention also provides, as reagents for precision therapy for γ-herpesvirus, a composition comprising one or more oligonucleotides able to hybridize to γ-herpesvirus circRNA in live tissue, such as lytically γ-herpesvirus-infected infected tissue of a diseased human or animal patient or tissue in vitro. Preferably, such oligonucleotides hybridize to their substrates/templates under "high stringency" conditions. Such oligonucleotides typically are DNA molecules, and they typically comprise between about 10 and about 30 nucleotides (such as 10, 11, 12, 13, 14, 15, 16, 17, 18, 19, 20, 21, 22, 23, 24, 25, 26, 27, 28, 29, or, 30 nucleotides). Exemplary sequences for such oligonucleotides include DP1-R: CGCCCGTATTCACACATTCC (SEQ ID NO:1), DP1-F: GACGCTAGTGCTGCATGGG (SEQ ID NO:2), DP2-F: TGAGGAATACCTCGTTGTCTTCCG (SEQ ID NO:3), DP2-R: AGCCCTTCTTCGTTATGCAC (SEQ ID NO:4), circvIRF4 R, CAAATGCATGGTACACCGAATAC (SEQ ID NO:5), and circvIRF4 F: GAACCGCTATTACAATGTTGGC (SEQ ID NO:6). Other oligonucleotides can be designed to hybridize to γ-herpesvirus circRNA. To this end, relevant template sequences are presented below in the Examples entitled "EXAMPLE 1-Epstein-Barr Virus (EBV) circRNA" and "EXAMPLE 2-Kaposi's Sarcoma-Associated Herpesvirus (KSHV) circRNA." Also, anti-sense oligo (ASO)-mediated targeting of circRNAs can be employed as a precision therapy option (see ncbi.nlm.nih.gov/pmc/articles/PMC5376066/, which is incorporated herein by reference). An embodiment of the invention provides a method of treating a condition associated with γ-herpesvirus infection in a mammal, the method comprising administering to the mammal any of the inventive oligonucleotides described herein to the mammal in an amount effective to treat or prevent the condition in the mammal.

For knock down of EBV in vivo and in vitro, an oligonucleotide targeting the BART small junction (SJ) sequence (TCGACGGGCAAGGTCCGGCGTGTC (SEQ ID NO:7)) or BART large junction (LJ) sequence (TCGACGGGCAAGATGCCATTGGGC (SEQ ID NO:8)) can be used. This sequence for the LJ is derived from the Akata strain. However, Exon II that has the large junction (LJ) (See FIG. 1) shows nucleotide polymorphism in different virus strains; thus, oligonucleotides targeting the large junction need to be designed accordingly. An exemplary oligonucleotide targeting the Small Junction has the following sequence: GACACGCCGGACCTTGCCCGUCGA (SEQ ID NO:9), wherein each of the nucleotides at positions 1-6 and 19-24 of SEQ ID NO: 9 contains 2'O-methylated ribose and each contiguous nucleotide of SEQ ID NO: 9 is connected by a phosphorothioate bond. A scrambled control having the same nucleotide content but different order can be used as a control to measure off-target effects. One exemplary scrambled control oligonucleotide is: AGCCUCGACCGTGACCGTGCAGCC (SEQ ID NO:10), wherein each of the nucleotides at positions 1-6 and 19-24 of SEQ ID NO: 10 contains 2'O-methylated ribose and each contiguous nucleotide of SEQ ID NO: 10 is connected by a phosphorothioate bond. Also, for the Akata strain, one exemplary oligonucleotide targeting the Large Junction has the following sequence: GCCCAATGGCATCTTGCCCGUCGA (SEQ ID NO:11), wherein each of the nucleotides at positions 1-6 and 19-24 of SEQ ID NO: 11 contains 2'O-methylated ribose and each contiguous nucleotide of SEQ ID NO: 11 is connected by a phosphorothioate bond. A scrambled control having the same nucleotide content but different order can be used as a control to measure off-target effects. One exemplary scrambled control oligonucleotide is: AGUCGTCTCGTCACGCAGGCCUAC (SEQ ID NO:12), wherein each of the nucleotides at positions 1-6 and 19-24 of SEQ ID NO: 12 contains 2'O-methylated ribose and each contiguous nucleotide of SEQ ID NO: 12 is connected by a phosphorothioate bond. For knock down of KSHV in vivo and in vitro, an oligonucleotide targeting the vIRF junction sequence (CATCTACCTCAGCCCCCGCGCCC (SEQ ID NO:13)) can be used. One exemplary oligonucleotide has the following sequence: GGGGCGCGGGGGCTGAGGUAGAUG (SEQ ID NO:14), wherein each of the nucleotides at positions 1-6 and 19-24 of SEQ ID NO: 14 contains 2'O-methylated ribose and each contiguous nucleotide of SEQ ID NO: 14 is connected by a phosphorothioate bond. A scrambled control having the same nucleotide content but different order can be used as a control to measure off-target effects. One exemplary scrambled control oligonucleotide is: GGCGGUGCGGCGTGAGGAAGGUGG (SEQ ID NO:15), wherein each of the nucleotides at positions 1-6 and 19-24 of SEQ ID NO: 15 contains 2'O-methylated ribose and each contiguous nucleotide of SEQ ID NO: 15 is connected by a phosphorothioate bond.

The oligonucleotides can be conjugated to other agents useful for precision therapy, such as antiviral agents, markers (e.g., radio-labled or fluorescent markers), or other desired agents. Also, the oligonucleotides can be analogues such as locked-nucleic acids or phosphorodiamidate morpholino oligomer (PMO) or short-hairpin RNA oligonucleotides. The oligonucleotides can be synthesized by standard methodology and then formulated in any suitable preparation, can be formulated in any suitable preparation, such as in lyophilized form (possibly including a lyoprotectant), or in solution, such as including buffers and preservatives or other antiviral or anticancer agents, if desired.

In use, the inventive oligonucleotide, including a composition comprising the oligonucleotide, can be delivered to a human or animal patient, preferably to a tumor or other tissue lytically infected with γ-herpesvirus. The oligonucleotide also can be employed in excised, infected tissue in vitro. Within the infected tissue, the inventive oligonucleotide binds to the circRNA, and/or to portions of the γ-herpesvirus genome encoding the circRNA, thereby altering production of the γ-herpesvirus circRNA, possibly interfering with the replication of the γ-herpesvirus within the tissue, and/or delivering any antiviral markers, markers (e.g., radio-labeled or fluorescent markers), or other desired agents conjugated to the oligonucleotide. The invention also provides a composition comprising the oligonucleotide and a pharmaceutically-acceptable carrier, examples of which are known in the art. Such compositions can be formulated for administration by any desired route, such as inhalation, injection (intratumorally, intraperitoneally, direct injection into a tumor, etc.), systemically, topically, etc.

Another embodiment of the invention provides a gene therapy vector comprising a circRNA and a gene of interest expressed under the control of a heterologous promoter.

The following technical Examples further illustrate the invention but, of course, should not be construed as in any way limiting its scope.

EXAMPLE 1-EPSTEIN-BARR VIRUS (EBV) circRNA

This Example demonstrates detection of EBV circRNA. Generally, this Example describes the identification of a locus expressing four circRNAs that are commonly present in EBV-positive post-transplant lymphomas, and are present in EBV-positive Burkitt lymphoma and spontaneous lymphoblastoid cell lines. This locus is lost in the cell-culture adapted B95.8 strain. Detection of EBV circRNA can be important for diagnosis and can be performed by simple rtPCR in fixed tissues. This locus may play an important and interesting role in EBV carcinogenesis and thus could be a target for precision therapies.

RNA sequencing was performed on exonuclease (RNaseR) treated EBV positive and negative post-transplant lymphoproliferative disease (PTLD) patient samples and identified EBV backspliced junctional reads within the RPMS1 locus only in EBV positive PTLD. These junctional reads were determined to be from circRNAs by RT-PCR using divergent primers. They are comprised of at least 4 differentially spliced isoforms that vary in size bases on specific combinations of intronic and exonic elements. In extended sampling, these viral circRNA were found in all 8 EBV+ but none of 9 EBV-PTLD tested. The presence of cRPMS1 in all EBV-positive cell lines tested also was verified, except the B95.8 line having a genetic loss of this locus. cRPMS1 are largely present during both latent and lytic replication, although some variation in relative quality exists during the viral life cycle and from cell line to cell line. circRNAseq analysis of KSHV-infected PEL cell lines also reveal several species of conserved viral circRNA which can also be detected in KS lesions.

Methods

RNA samples were extracted from EBV positive and EBV negative PTLD tumor samples and submitted for circRNA sequencing using Illumina HiSeq PE150. Sequencing results were evaluated by three different algorithms: CIRI2 (Gao Y et al., Genome Biology 2015, 16:4, Gao Y et al., Briefings in Bioinformatics, 2017, 1-8) (incorporated herein in its entirety by reference), circ_finder (Zhang et al., Molecular Cell 2013, 51:792-806) (incorporated herein in its entirety by reference), and CIRCexplorer2 (Zhang et al., Cell 2014, 159:134-147) (incorporated herein in its entirety by reference).

The initial analysis indicated junction reads from eight circRNA candidates of the positive strand corresponding to RPMS1 (BART), BSLF1, BKRF3/4, BALF4/A73, and LMP1 regions (Table 3). For most of these circRNAs only one or two junction reads were detected. However, for RPMS1 region, 4-12 junction-reads were identified by different algorithms. Additionally, a circRNA from BHLF1 was detected during lytic induction (Table 2).

Divergent and convergent primer pairs (DP1-R (reverse): CGCCCGTATTCACACATTCC (SEQ ID NO:1) and DP1-F (forward): GACGCTAGTGCTGCATGGG (SEQ ID NO:2)) were designed to further analyze the circular RNA from BART region (circBART) by diagnostic and qRT-PCR. PCR with divergent primers (Primer number 6860-6861, circRNA maps) revealed two different junction sequences and convergent primers indicated presence of four different circular RNAs (circRNA maps). These findings were verified in a number of EBV-infected PTLD patient samples and also in Akata, Daudi, and Raji cell lines, but not in EBV negative PTLD samples and B95.8 cell line which has a deletion in this area. Sequencing analysis of the entire circRNA region showed single nucleotide polymorphisms among different strains. An example from Akata strain together with circRNA maps are given in FIGS. 2A-2B, 3A-3B, 4A-4B, and 5A-5B. Table 1 is a summary of the results obtained from three different circRNA analysis algorithm using genome annotation of the Mutu strain.

TABLE 1

Summary of the results obtained from three different circRNA analysis algorithm using genome annotation of the Mutu strain

| | circRNA-start | circRNA-end | strand | circRNA reads | Junction sequence |
|---|---|---|---|---|---|
| chrEBV (Mutu) | 72584 | 72994 | + | 1 | GTTTGTGTCTGTGCTGCAGAAGCTCATGGG CCTAACGGCCTGCCTGCGCCGCATGCGTCA CAAGATCAAAGAGATTGGGGCCCCGCTTTT TGACAGCGTAATCCCCGGCTTCCGGTCTGC AACCTGGTCCTGGACCTGGATCTAAAGATC AAGGGGCCCCCTGGTCGCTGGAGGAAATC TATGACCTGTGCCGGACCGTGCGGCGTGAG GTACTGCGCCTCATGCGCCGCCTGGGTCCA GTGTCCAGGGCCCACCCAGTCTATTTTTTC AAATCAGCTTGTC (SEQ ID NO: 69) |
| chrEBV (Mutu) | 98689 | | + | 1 | GTCACTCACGTCCTCCTCCTGGATAGACTG GGAGGCCTGAGACCCCAGAGTGTAGCTGCT GCTCTGTGAAGTCTCTTCCTCCTCGTCCGA CAAGAGGCGCCGGTCCCTGCAAGACCGGAC CCCACGCGACTTCAGAAACATGGCCATAGT GATGACCCCTCTACAGCCTCCAAAGTCAGA CTCGTCTGAATCTGAAGGATGCCACGAGGG GTCGCTATCACTGCCCTCAGATGGGTCTTC GTCACTGGGGTACTCTTCCTCCAAATCAAT CTCC (SEQ ID NO: 70) |
| chrEBV (Mutu) | 140423 | 146196 | + | 2 | GGCGGGTAGTTATTGGCTCCGAGATTCTAG AAACACGTGTCCCGCTGACGCAGGGGGCCT TGCTTCCCCTGTTATTCTGATAGAATGACA GCCTGTAACACAAAGTGGAAGCAGCACTTA TCAGCGTTGGAGGCACGGGGGCAAAGGTCA AGTAGCTGCGTCCAAATTCAGCTCAGTGAC ACGTCCAACGGCATATCACGTGTATGTG (SEQ ID NO: 71) |
| chrEBV (Mutu) | 146094 | 150210 | + | 1 | GCCGGACCTGTAACACAAAGTGGAAGCAGC ACTTATCAGCGTTGGAGGCACGGGGGCAAA GGTCAAGTAGCTGCGTCCAAATTCAGCTCA GTGACACGTCCAACGGCATCTTGCCCGTCG ACGAGCTCCGGCCATGGCCGAAGCTTACCC (SEQ ID NO: 72) |
| chrEBV (Mutu) | 149442 | 150210 | + | 4-12 | GCACTCTGACCAGGACATCGTGCTAAGCGT CCTGAATCCGCGCAGCCTGCTGGCGCAGCA CACGCCCCCATTTCTAAAGTCATACGCCCG TATTCACACATTCCCGGGGAAGGTGTGTCC GGTCAACGCCATACGCCGCGGTAAGGGCTA CGTCCGAGTCTCCGTGGACACGCCGGACCT TGCCCGTCGACGAGCTCCGGCCATGGCCGA AGCTTACCCCGGAGGAGCCCATGCAGCACT AGCGTCCCGGCGCTCGTCGTTC (SEQ ID NO: 73) |
| chrEBV (Mutu) | 156497 | 158618 | + | 2 | GGTTTGTTTAGCAGCCTGGTCTCGGGTTTC ATCTCCTTCTTCAAAAACCCCTTCGGCGGC ATGCTCATTCTGGTCCTGGTGGCGCCTACC GCCACGCGTCAGCAAACCAGCTTTCCTTTC CGAGTCTGCGAGCTCTCCAGCCACGGCGAC CTGTTCCGCTTCTCCTCGGACATCCAGTGT CCCTCGTTTGGCACGCGGGAGAATCACACG GAGGGCGGGACGAACAGCGTGCCTCCAACG TCTTTGACCTGGAGGGCATC (SEQ ID NO: 74) |
| chrEBV (Mutu) | 163120 | 163977 | + | 1 | GCATTGTGGAACACGTAGATGTCCCTGTGA TAGGAGGTAGCGCGTAGGAGCCCGCAGTTG GGGTCGGGCCTCCTGTGCAGAGCCTTGACA TGGTTGACTTCGAGACCCCCGAGACGTAGA GGACGGAATTGGTGGCAAAGATCTGCGTGG CCACCTTGGCCTGGTCCTGCAGGCTCTGCT TCTCCAGCAGCTCCACCAGCTTGCCCACCC GTCGGACGCGCAGCGCCTGCGCCAGCCCGG TGTACAGCGCCTCGTGCATGCAGCGGCTGA GGTCCGAGTTGTAAAACTGGC (SEQ ID NO: 75) |

TABLE 1-continued

Summary of the results obtained from three different circRNA analysis algorithm using genome annotation of the Mutu strain

| | circRNA-start | circRNA-end | strand | circRNA reads | Junction sequence |
|---|---|---|---|---|---|
| chrEBV (Mutu) | 168084 | 169413 | + | 1 | AGTCCACTTGGAGCCCTTTGTCTACTCCTA CTGATGAGTAAGTATTACACCCTTTGCCCC ACACCCCCTTTCCCTTACTCTTCCTTCTCT AACGCACTTTCTCCTCTTTCCCCAGTCACC CTCCTGCTCATCGCACTCTGGATTTTTCGA CATGGACAACGACACAGTGATGAACACCAC CACGATGACTCCCTCCCGCACCCTCAACAA GCTACCGATGATTCTAGCCATGAAATTCCC ATCTCCGCCGTCTGCTGCTTCGTCACCCGC (SEQ ID NO: 76) |

TABLE 2 circRNA genome coordinates and junction read counts identified in PTLD tumor samples (R1235, R1243) and BC1 cell line treated with DMSO or NaB/TPA for lytic activation

| Sample name | | circRNA_start | circRNA_end | #junction reads | #non_junction reads | junction_reads ratio | circRNA_type | gene_id | strand |
|---|---|---|---|---|---|---|---|---|---|
| PTLD | R1235 | 140423 | 146196 | 2 | 239 | 0.016 | intron | RPMS1 | + |
| | | 149443 | 150210 | 12 | 126 | 0.16 | exon | RPMS1 | + |
| | R1243 | 146095 | 150210 | 12 | 1269 | 0.019 | intron | RPMS1 | + |
| | | 149443 | 150210 | 49 | 1365 | 0.067 | exon | RPMS1 | + |
| BC1 | DMSO | 39880 | 40171 | 20 | 10640 | 0.004 | exon | BHLF1 | − |
| | | 146095 | 150210 | 61 | 4447 | 0.027 | intron | RPMS1 | + |
| | | 149443 | 150210 | 143 | 5009 | 0.054 | exon | RPMS1 | + |
| | | 149443 | 159779 | 3 | 3391 | 0.002 | exon | RPMS1 | + |
| | | 155128 | 159779 | 41 | 3176 | 0.025 | exon | RPMS1 | + |
| | | 155128 | 166318 | 2 | 2446 | 0.002 | intergenic | n/a | + |
| | | 156388 | 158612 | 5 | 3576 | 0.003 | exon | A73, BALF4, BALF3 | + |
| | NaB/TPA | 1026 | 1682 | 3 | 52 | 0.103 | exon | LMP-2A, LMP-2B | + |
| | | 39880 | 40171 | 56 | 44965 | 0.002 | exon | BHLF1 | − |
| | | 146095 | 150210 | 17 | 211 | 0.139 | intron | RPMS1 | + |
| | | 149443 | 150210 | 39 | 288 | 0.213 | exon | RPMS1 | + |
| | | 155128 | 159779 | 7 | 347 | 0.039 | exon | RPMS1 | + |

EXAMPLE 2-KAPOSI'S SARCOMA-ASSOCIATED HERPESVIRUS (KSHV) circRNA

This Example demonstrates detection of KHSV circRNA. Generally, this Example describes the identification of two loci expressing circRNAs in KSHV positive primary effusion lymphoma cell lines by RNA-seq analysis. The results obtained in the series of experiments discussed in this Example are surprising and unexpected, since the tissue sample was over 30 years old at the time of the assays. It is, in this context, well-known that RNA degrades quickly; therefore the detection of KHSV circRNA in a 30+-year-old tissue sample is remarkable.

Detection of KSHV circRNA may be important for diagnosis and can be performed by simple reverse transcription PCR. Expression of these circRNAs may play a critical role in KSHV carcinogenesis and virus life cycle, and thus could be a target for precision therapies.

Methods

RNA samples were extracted from latent or lytic induced KSHV positive primary effusion lymphoma cell lines and submitted for circRNA sequencing using Illumina HiSeq PE150. Sequencing results were evaluated by CIRI2 (Gao Y et al., Genome Biology 2015, 16:4 (incorporated herein in its entirety by reference), Gao T et al., Briefings in Bioinformatics, 2017, 1-8 (incorporated herein in its entirety by reference)).

The initial analysis indicated junction reads from circRNA candidates from two different loci viral IRF4 (vIRF4) and PAN (Table 3). For most of the PAN/K7 region circRNAs less than 11 junction reads were detected. However, for vIRF4 region, 32-439 junction-reads were found in three different cell lines BC1, BCBL1 and BCP1.

Divergent primers (6941 and 6943) (circvIRF4 R (reverse): CAAATGCATGGTACACCGAATAC (SEQ ID NO:5) and circvIRF4 F (forward): GAACCGCTATTA-CAATGTTGGC (SEQ ID NO:6)) were designed to detect the junction reads for circ-vIRF4 and verified the sequencing results from PEL cell lines. Distinct from circ-vIRF4, the number and localization of circRNAs detected from PAN/K7 region showed variations in different cell lines (Table 3). Examples of the circRNA sequences are given in FIGS. 6A-7I. Examples for circRNAs identified from KSHV PAN/K7 region are shown in FIGS. 7A-7I.

TABLE 3

List of circRNAs identified in latent KSHV positive primary effusion lymphoma (PEL) cell lines

| | chr | circRNA_start | circRNA_end | #junction_reads | gene_id/region | strand |
|---|---|---|---|---|---|---|
| BCBL1-DMSO | HQ404500.1 (BCBL1) | 28198 | 29016 | 10 | PAN | − |
| | | 28273 | 28593 | 6 | PAN | − |
| | | 28273 | 28614 | 2 | PAN | − |
| | | 28273 | 28624 | 4 | PAN | − |
| | | 28273 | 28691 | 9 | PAN | − |
| | | 28273 | 29016 | 2 | PAN | − |
| | | 28290 | 28593 | 2 | PAN | − |
| | | 28406 | 29044 | 7 | PAN | + |
| | | 28519 | 29016 | 2 | PAN | − |
| | | 28692 | 29016 | 6 | PAN | − |
| | | 87690 | 88321 | 32 | vIRF4 region | − |
| BCP1-DMSO | HQ404500.1 (BCBL1) | 28273 | 28518 | 5 | PAN | − |
| | | 28273 | 28531 | 4 | PAN | − |
| | | 28273 | 28593 | 11 | PAN | − |
| | | 28273 | 28614 | 9 | PAN | − |
| | | 28273 | 28691 | 4 | PAN | − |
| | | 28273 | 28695 | 8 | PAN | − |
| | | 28273 | 28717 | 2 | PAN | − |
| | | 28273 | 28733 | 3 | PAN | − |
| | | 28273 | 28807 | 3 | PAN | − |
| | | 28273 | 28819 | 5 | PAN | − |
| | | 28273 | 29016 | 8 | PAN | − |
| | | 28290 | 28593 | 6 | PAN | − |
| | | 28290 | 28717 | 3 | PAN | − |
| | | 28406 | 28721 | 9 | PAN | + |
| | | 28420 | 28695 | 7 | PAN | − |
| | | 28519 | 29016 | 21 | PAN | − |
| | | 28692 | 29016 | 3 | PAN | − |
| | | 87690 | 88321 | 439 | vIRF4 region | − |
| BC1-DMSO | HQ404500.1 (BCBL1) | 28273 | 28593 | 2 | PAN | − |
| | | 28519 | 29016 | 5 | PAN | − |
| | | 87690 | 88321 | 92 | vIRF4 region | − |
| | | 117854 | 122054 | 36 | miRNA region | − |
| | | 117854 | 122169 | 206 | miRNA region | − |

EXAMPLES 3-8

The following materials and methods were employed in the experiments described in Examples 3-8.

Tumor Samples and Cell Lines

Seventeen tissue specimens from patients with PTLD, one EBV-positive AIDS-associated lymphoma, three Kaposi's sarcoma (KS 1 to 3), and MCD were obtained as byproducts of diagnostic or therapeutic procedures performed at Columbia University College of Physicians & Surgeons and at the University of Pittsburgh Medical Center (UPMC) with approval of the Institutional Review Board. These specimens were deidentified before use in this study. Seven pathologically confirmed tissue specimens were obtained from AIDS and Cancer Specimen Resource (ACSR) (KS 4 to 10). Tissues were snap-frozen and stored in liquid nitrogen until use. Assignment of EBV viral status for PTLDs was based on pathology reports and, in one case, based on poly(A) RNA sequencing (PTLD12). Tumor sections from two NPC patient-derived xenograft tumor models, C15 and C17 (Busson P, et al. (1988) Int J Cancer 42:599-606), were kindly provided by Nancy Raab-Traub, University of North Carolina.

EBV-positive Daudi, Raji, and B95-8; KSHV and EBV coinfected BC1; KSHV-positive BCBL1; and EBV/KSHV-negative BJAB cell lines were obtained from the American Type Culture Collection (ATCC). EBV-positive sLCL (Gottschalk S, et al. (2001) Blood 97:835-843) was a generous gift from Cliona Rooney, Texas Children's Hospital. Cells were maintained in Roswell Park Memorial Institute (RPMI) 1640 (Cellgro) supplemented with 10% FBS (VWR Seradigm). Recombinant Akata and the HK1 NPC cell line infected with recombinant Akata strain (Lo AK, et al. (2006) Neoplasia 8:173-180) were maintained with $800_1$g/mL of neomycin selection in RPMI supplemented with 10% FBS. BC1, BCBL1, Daudi, Raji, and BJAB cell lines were authenticated by the University of Arizona Genetics Core Facility. The Akata and sLCL cell lines showed unique profiles with no matches to any reference in any database and thus were determined not to be contaminated with known cell lines.

For lytic reactivation, BJAB and KSHV-positive BC1 and BCBL1 cells were incubated with 20 ng/mL of TPA and 3 mM NaB for 48 h; EBV-positive cell lines were incubated with 20 ng/mL of TPA and 5 mM NaB for 48 h. Efficiency of lytic reactivation was measured by qRT-PCR analysis of immediate early (ORF50, ORF39), early (K8, ORF37), and latent (v-cyclin, viral interleukin 6, vIL6) viral transcript expression.

For the viral transcript expression analysis of BC1 and BCBL1 cell lines, KSHV (+) primary effusion lymphoma lines were treated with NaB/TPA for 48 h. Extracted RNA was used for Ribominus, RnaseR+RNA sequencing. cDNA generated from these RNA was analyzed for immediate early (ORF50, ORF39), early (K8, ORF37) and latent (v-cyclin) transcript expression profile to assess the reactivation efficiency.

RNA Isolation, Poly(A)+RNA Sequencing, and circRNA Sequencing

Total RNA was isolated from tumor samples and cell lines using TRIzol (Ambion) followed by treatment with TURBO DNase (Thermo Fisher). RNA quality was confirmed by Agilent TapeStation (Children's Hospital of Pittsburgh of UPMC, sequencing core facility) and by Agilent 2100 Bioanalyzer (CD Genomics). RNA integrity numbers (RIN) were between 1.9 and 2.1 (A260/280), and RIN was ≥7.5 for all samples, except BC1$^{NaB/TPA}$, BCBL1$^{NaB/TPA}$, and PTLD9 (RIN≥5.7 to 7.3). For poly(A)+RNA sequencing of PTLD samples, Ion Torrent adapter-ligated libraries were prepared from extracted RNA according to the Ion Total RNA-seq Kit (Life Technologies) following the manufacturer's instructions and sequenced using Ion PGM sequences at the Children's Hospital of Pittsburgh of UPMC, sequencing core facility. For circRNA sequencing, ribosome-depleted and RNase R-treated RNA samples were used for library preparation and subsequently sequenced using Illumina HiSeq platform in PE150 sequencing mode (CD Genomics). The accession number for the sequencing data reported here is Gene Expression Omnibus database GSE117798.

Bioinformatic Analysis

Raw FastQ files were trimmed with Trim Galore, (bioinformatics.babraham.ac.uk/projects/trim_galore/) using the following parameters: q=25, e=0.1, and length=50, and the quality control was performed with FastQC tool. CIRI2 algorithm was used for viral and human circRNA prediction (Gao Y, et al. (Feb. 28, 2017) Brief Bioinform, 10.1093/bib/bbx014)//sourceforge.net/projects/ciri/files/CIRI2/) with the default settings. In addition to CIRI2, the CIRCexplorer (Zhang XO, et al. (2016) Genome Res 26:1277-1287.) (github.com/YangLab/CIRCexplorer2) algorithm was used to confirm viral circRNA predictions. RNA-seq reads were aligned to GRCh37 (Hg19; University of California, Santa Cruz Genome Browser), BCBL1 (HQ404500), and Mutu (KC207814) reference genomes using BWA or STAR mappers. Human circRNAs were further analyzed using circBASE (58) to annotate the identified circRNAs in PTLD samples and PEL cell lines.

CLC genomics workbench (Qiagen) was used to align RNA-seq reads to GRCh37 (Hg19), BCBL1 (HQ404500), and Mutu (KC207814) reference genomes and to visualize additional annotation. DMSO-treated poly(A) RNA sequencing data for BCBL1 cell lines (SRX2323239, Zhou F, et al. (2017) Mol Cancer Ther 16:2627-2638) were obtained from National Center for Biotechnology Information's Gene Expression Omnibus website.

Potential splice acceptor and donor site analysis was done using Human Splicing Finder (V3.1) (Desmet F O, et al. (2009) Nucleic Acids Res 37:e67). Venn diagrams were generated using Biovenn (Hulsen T, et al., BMC Genomics 9:488) and nVenn (Pérez-Silva J G, et al. (2018) nVenn: Bioinformatics 34:2322-2324) programs.

RNase R Treatment and RPAD

To obtain highly purified circRNAs, 2 µg of RNA was treated with 8 units (U) RNase R (Lucigen) in 1×Rnase R buffer at 37° C. for 30 min. The reaction mixture was heat-inactivated at 65° C. for 20 min or the RNA was precipitated using sodium acetate/ethanol supplemented with 20 µg of glycogen as a carrier. This was followed by polyadenylation (E-PAP, AM1350; Thermo Fisher) with a subsequent poly(A)+RNA depletion using Poly(A)Purist MAG Kit (AM1922; Thermo Fisher) (RPAD protocol) as described by Panda et al. (Panda A C, et al. (2017) Nucleic Acids Res 45:e116).

cDNA Synthesis, RT-PCR, and qPCR

One microgram of DNase digested RNA was either treated or untreated with Rnase R and reverse-transcribed using SuperScript IV (Thermo Fisher) with random hexamers in a total volume of 20 µL, according to the manufacturer's protocol. All RT-PCRs were performed using 1/40 of the cDNA, Q5 high-fidelity polymerase (NEB) or standard Taq polymerase (NEB). Q5 PCR reactions were performed at the following conditions: initial denaturation at 98° C. for 2 min; followed by 35 cycles of denaturation at 98° C. for 10 s, based on the primer pairs annealing at 65° C. to 71° C. for 30 s; extension at 72° C. for 30 s/kb; and a final extension at 72° C. for 5 min. For standard Taq polymerase supplemented with Thermopol buffer (NEB), initial denaturation was performed at 95° C. for 3 min; followed by 25 to 30 cycles of denaturation at 95° C. for 15 s, annealing at 56° C. for 30 s; and extension at 68° C. for 60 s/kb and a final extension at 68° C. for 5 min. As needed, RT-PCR products were gel-extracted and cloned into TOPO-TA vector (Invitrogen) according to the manufacturer's recommendations.

Synthesized cDNA was analyzed by qPCR using SYBR Green PowerUp Master Mix according to the manufacturer's instructions (Thermo Fisher). The determined threshold cycle (Ct) values were used to calculate the mRNA fold changes of the NaB/TPA-treated versus DMSO-treated cells using the delta-delta Ct method. The Ct values of GAPDH were used as reference. PCR primers [Integrated DNA Technologies (IDT)] are listed in Table 10.

EBV DNA copy number was determined by the SYBR green (Thermo Fisher) qPCR absolute quantitation method using a BALFS plasmid as template for the standard curve. The linear limits of detection were between 4 and $4 \times 10^8$ copies per reaction. Reactions were assembled as previously described (Caves E A, MSphere 3:e00152-18). Input genomic DNA was normalized and compared with a reference cell line (Raji) averaging 50 EBV episomal copies per cell. EBER-positive PTLD8 and PTLD10 measured two and seven copies per cell, respectively. EBER-negative PTLD13, PTLD15, and PTLD16 samples measured 7, 14, and 0.05 copies per cell, respectively. Sample PTLD16 may contain EBV-infected infiltrating B lymphocytes and is more similar in value to the EBER-negative and circRNA negative PTLD7 measuring 0.001 copy per cell.

Oligonucleotide-Targeted RNase H Cleavage

ASOs were designed against the unique junction sites for each viral circRNA and contain phosphorothioate linkages for increased stability as well as six nucleotides at each end containing 2'-O-methylated ribose for exo/endonuclease resistance. HPLC purified (with Na+ salt exchange) ASOs were obtained from IDT. For in vitro RNase H assays, 2 µg of RNA was incubated with 0.4 µg of ASO in 1×RNase H buffer at 37° C. for 20 min. Subsequently, 1 U RNase H (NEB) was added, followed by incubation for an additional 40 min. RNA was purified either using Qiagen RNeasy columns or by sodium acetate/ethanol precipitation with 20 µg of glycogen as carrier. ASO and scrambled controls (IDT) are listed in SI Appendix, Table 10.

Nuclear/Cytoplasmic Fractionation

Nuclear/cytoplasmic fractionation was performed from $1 \times 10^7$ BC1 cells using the NR-PER Nuclear and Cytoplasmic Extraction Reagent (Pierce), according to the manufacturer's protocol. One microgram of total RNA from each fraction was used for cDNA synthesis, and expression level of the indicated circRNAs in each fraction was analyzed. The quality of the fractionation assay was controlled by immunoblotting for a nuclear marker (Lamin A/C; Cell Signaling) and a cytoplasmic marker (LAMP-1; eBioscience).

Polysome Fractionation

BC1 cells were incubated with 100 μg/mL of cyclohex- imide (CHX) for 15 min, harvested, rinsed with ice-cold PBS-CHX, and lysed in 500 μL of polysome lysis buffer (10 mM Hepes pH 7.4, 0.5% Nonidet P-40, 100 nM KCl, 5 nM MgCl2) freshly supplemented with CHX, and protease inhibitor Ribolock RNase Inhibitor (Thermo Fisher). After centrifugation (15 min at 17,000×g), the cytoplasmic lysates (1 mg of lysate in <400-μL volume) were loaded onto 10 to 50% (wt/vol, 0.9 mL) linear sucrose gradients (10 mM Hepes pH 7.4, 100 mM KCl, 5 mM MgCl2). Gradients were centrifuged for 3 h at 145,000×g (35,000 rpm in a Sorvall AH-650 rotor), followed by collection of 12×0.5 mL fractions. RNA was extracted from the collected fractions as described in RNA Isolation, poly(A)+RNA Sequencing, and circRNA Sequencing using TRIzol LS reagent (Ambion) and treated with DNase before cDNA synthesis and qRT-PCR. Using the qPCR cycle threshold (Ct) values, the percent distribution for the mRNAs across the gradients was calculated using the delta Ct method (Panda A C, et al., (2017) Bio Protoc 7:e2126).

EXAMPLE 3

This example demonstrates the sequencing of EBV circRNA.

RNA sequencing was performed with two EBV-negative (PTLD4 and PTLD5) and two EBV-positive PTLD (PTLD6 and PTLD9) samples using polyA+-selected or RNase R-treated RNA libraries (Tables 4-7). RNase R is an exoribonuclease that selectively depletes linear RNAs and enriches circular or lariat RNAs. Back-spliced junctions (BSJ), based on EBV genome Mutu sequence (KC207814) were identified using the CIRI2 circRNA prediction algorithm (Gao Y et al., (2017) Brief Bioinform, Gao Y et al., (2015) Genome Biol 16:4). EBV positive PTLD patient samples each showed two circRNA BSJ candidates from the BART locus: BSJ1 (Mutu: 146,095-150,210) and BSJ2 (Mutu: 149,443-150,210) (Tables 4-7).

For the identification of EBV RNase R-resistant RNAs, comparison of poly(A)$^+$-RNA (PTLD9$^{polyA+seq}$) and RNase R-treated RNA (PTLD9$^{RNaseR+seq}$) from an EBV-positive PTLD sample (PTLD9) revealed RNase R-resistant RNAs that are potential back-spliced junctions (BSJ) of circular RNAs. CIRI2 analysis using EBV Mutu genome KC207813 identified a minority of these reads to encode actual EBV BSJs (Tables 6-7). An expanded view of the BART (RPMS1) region (146-150,2 kb) encoding the highest concentration of EBV BSJs revealed low mRNA but high RNase R-resistant RNA abundance.

BART-BSJ1 results from the fusion of the 3' end of exon IV with the 5' end of exon II. BART-BSJ2 is formed by the fusion of the 3' end of exon IV with the 5' end of exon IIIa. EBV mirBART 7-22 miRNAs encoded by intron 2 were spliced out from the circBARTs. Potential acceptor and donor splice sites within the BART region were examined using Human Splicing Finder 3.1 (Desmet F O, et al. (2009) Nucleic Acids Res 37(9):e67) which showed high entropy scores for canonical splice sites, including those flanking introns 3a and 3b, as well as for BART-BSJ2 supporting the occurrence of this backsplicing event. BART BSJ1 and BSJ2 junction reads were also sequenced from RNase R-treated RNA of the EBV and KSHV-co-infected BC1 cell line with or without sodium butyrate-phorbol ester (NaB/TPA) induction of viral lytic replication (Dresang L R, et al. (2011) BMC Genomics 12:625) (Tables 4-7)

For the identification of EBV backsplice junctions in BC1 cells, ribominus and RNase R-treated RNA sequencing reads from EBV and KSHV co-infected BC1DMSO and BC1NaT/TPA samples were mapped to the EBV reference genome (Mutu strain: KC207813) and read coverage files were generated using CLC Genomics Workbench tool. EBV mRNA and non-coding RNA (ncRNA) between genome position 146-150.2 kb corresponded to BART exons II-IV flanking the intronic region with the miRNAs (mirBART 7-22). BSJ1 was formed by backsplicing of the 3' end of exon IV onto the 5' end of exon II. BSJ2 was formed by 3' end exon IV backsplicing onto end of exon IIIa.

TABLE 4

| | | | BC1-DMSO | | | |
|---|---|---|---|---|---|---|
| circRNA_ID | circRNA_start | circRNA_end | strand | #junction_reads | SM_MS_SMS | #non_junction_reads |
| chrEBV(Mutu): 360\|1682 | 360 | 1682 | + | 3 | 2_2_0 | 4 |
| chrEBV(Mutu): 3304\|4348 | 3304 | 4348 | − | 4 | 2_2_0 | 98 |
| chrEBV(Mutu): 39880\|40171 | 39880 | 40171 | − | 19 | 10_10_0 | 10640 |
| chrEBV(Mutu): 146095\|150210 | 146095 | 150210 | + | 62 | 11_12_26 | 4447 |
| chrEBV(Mutu): 149443\|150210 | 149443 | 150210 | + | 138 | 46_25_41 | 5009 |
| chrEBV(Mutu): 149443\|159779 | 149443 | 159779 | + | 4 | 1_1_2 | 3391 |
| chrEBV(Mutu): 155128\|159779 | 155128 | 159779 | + | 41 | 4_9_16 | 3176 |
| chrEBV(Mutu): 155128\|166318 | 155128 | 166318 | + | 2 | 1_2_1 | 2446 |
| chrEBV(Mutu): 156388\|158612 | 156388 | 158612 | + | 5 | 2_0_1 | 3576 |

TABLE 4-continued

BC1-DMSO

| circRNA_ID | junction_reads_ratio | gene_id | RPM |
|---|---|---|---|
| chrEBV(Mutu): 360\|1682 | 0.6 | LMP-2B, LMP-2A | 6.96212373 |
| chrEBV(Mutu): 3304\|4348 | 0.075 | BNRF1 | 9.28283163 |
| chrEBV(Mutu): 39880\|40171 | 0.004 | BHLF1 | 44.0934503 |
| chrEBV(Mutu): 146095\|150210 | 0.027 | RPMS1/BART | 143.88389 |
| chrEBV(Mutu): 149443\|150210 | 0.054 | RPMS1/BART | 320.257691 |
| chrEBV(Mutu): 149443\|159779 | 0.002 | RPMS1/BART | 9.28283163 |
| chrEBV(Mutu): 155128\|159779 | 0.025 | RPMS1/BART | 95.1490243 |
| chrEBV(Mutu): 155128\|166318 | 0.002 | RPMS1/BART | 4.64141582 |
| chrEBV(Mutu): 156388\|158612 | 0.003 | RPMS1, A73, BALF4, BALF3 | 11.6035395 |

TABLE 5

BC1-NaB_TPA

| circRNA_ID | circRNA_start | circRNA_end | strand | #junction_reads | SM_MS_SMS |
|---|---|---|---|---|---|
| chrEBV(Mutu): 1026\|1682 | 1026 | 1682 | + | 3 | 1_0_2 |
| chrEBV(Mutu): 39880\|40171 | 39880 | 40171 | − | 57 | 22_23_0 |
| chrEBV(Mutu): 146095\|150210 | 146095 | 150210 | + | 17 | 4_3_9 |
| chrEBV(Mutu): 149443\|150210 | 149443 | 150210 | + | 39 | 14_5_14 |
| chrEBV(Mutu): 155128\|159779 | 155128 | 159779 | + | 7 | 2_1_2 |

| circRNA_ID | #non_junction_reads | junction_reads_ratio | gene_id | RPM |
|---|---|---|---|---|
| chrEBV(Mutu): 1026\|1682 | 52 | 0.103 | LMP-2A, LMP-2B | 2.30579092 |
| chrEBV(Mutu): 39880\|40171 | 44965 | 0.002 | BHLF1 | 43.8100274 |
| chrEBV(Mutu): 146095\|150210 | 211 | 0.139 | RPMS1/BART | 13.0661485 |
| chrEBV(Mutu): 149443\|150210 | 288 | 0.213 | RPMS1/BART | 29.9752819 |
| chrEBV(Mutu): 155128\|159779 | 347 | 0.039 | RPMS1/BART | 5.38017881 |

TABLE 6

PTLD9

| circRNA_ID | circRNA_start | circRNA_end | strand | #junction_reads | SM_MS_SMS |
|---|---|---|---|---|---|
| chrEBV(Mutu): 146095\|150210 circBART_1 | 146095 | 150210 | + | 9 | 3_3_10 |
| chrEBV(Mutu): 149443\|150210 circBART_2 | 149443 | 150210 | + | 33 | 25_13_20 |

| circRNA_ID | #non_junction_reads | junction_reads_ratio | gene_id (RPM) |
|---|---|---|---|
| chrEBV(Mutu): 146095\|150210 circBART_1 | 1269 | 0.019 | RPMS1/BART (61.3) |
| chrEBV(Mutu): 149443\|150210 circBART_2 | 1365 | 0.067 | RPMS1/BART (224.7) |

TABLE 7

| | | | PTLD6 | | |
|---|---|---|---|---|---|
| circRNA_ID | circRNA_start | circRNA_end | strand | #junction_reads | SM_MS_SMS |
| chrEBV(Mutu):146095\|150210 circBART_1 | 146095 | 150210 | + | 1 | |
| chrEBV(Mutu):140423\|146196 (only CIRI2) | 140423 | 146196 | + | 2 | 2_0_2 |
| chrEBV(Mutu):149443\|150210 circBART_2 | 149443 | 150210 | + | 12 | 7_5_3 |

| circRNA_ID | #non_junction_reads | junction_reads_ratio | gene_id (RPM) |
|---|---|---|---|
| chrEBV(Mutu):146095\|150210 circBART_1 | | | RPMS1/BART (37.0) |
| chrEBV(Mutu):140423\|146196 (only CIRI2) | 239 | 0.016 | RPMS1/BART |
| chrEBV(Mutu):149443\|150210 circBART_2 | 126 | 0.16 | RPMS1/BART (444.5) |

EXAMPLE 4

This example demonstrates the characterization of EBV circBARTs in EBV cell lines.

BSJ1 and BSJ2 junction reads of putative circBART_1 and circBART_2 candidates were identified at relatively high levels in both EBV-positive PTLDs (61.3- 224.7 RPM, Tables 4-7) and in latent BC1 cells (between 144-320.3 RPM, Tables 4-7). Therefore, two junction-spanning divergent primer pairs were designed (DP1 and DP2) to further confirm and characterize these circRNAs in different cell lines by reverse-transcriptase (RT) PCR. The DP2 primer pair amplified four bands ranging between 400-700 bp from PTLD6, BC1 and Akata cell RNAs, which were confirmed by cloning and sequencing. CircBART_1.1 (711 nt) and circBART_1.2 (501 nt) contain exons II, IIIa, IIIb and IV and form the BSJ1 between exons II and IV upon backsplicing. CircBART_2.1 (609 nt) and circBART_2.2 (399 nt) lack exon II and form the BSJ1 between exons IIIa and IV. In circBART_1.1 and circBART_2.1, intron 3a between exons Ma and Mb was additionally retained.

EBV circBART_1 and circBART_2 expression was further examined in RNAs from cell lines having various forms of EBV latency. Daudi, Akata, and BC1 have Type I EBV latency, whereas PTLD-derived cell lines spontaneously-immortalized by EBV (sLCL) express Type III latency and marmoset B95-8 is an EBV producer cell line (Miller G & Lipman M (1973) Proc Natl Acad Sci U S A 70(1):190-194). HK1EBV cells were derived by infecting the EBV-negative HK1 nasopharyngeal carcinoma cell line with the EBV Akata strain and have Type II latency. Three to four bands were detected migrating between 400-700 bp in all samples except the EBV-uninfected HK1 control cells and the B95-8 cell line which has a 12-kb deletion within the BART locus (Raab-Traub N, et al. (1980) Cell 22(1 Pt 1):257-267) from position 139,724 to 151,554 (NC_007605). Junction spanning DP1 primers amplified bands migrating at 162 bp (BSJ2 of circBART_2.1 and 2.2) and 264 bp (BSJ1 of circBART_1.1 and 1.2). In contrast to circBARTs, linear viral (LMP2) and cellular (GAPDH) transcripts were diminished following RNase R treatment. The DP2 primer pair identified all four circBART forms, and the DP1 primer pair identified only the two backsplice junctions representing paired circBARTs. Convergent primers were used to measure viral LMP2 and cellular GAPDH mRNA transcripts. RNA from EBV uninfected HK1 and the B95-8 cell line, having a deletion of the BART locus, were used as negative controls.

EXAMPLE 5

This example demonstrates the characterization of circBARTs in EBV malignancies.

RNA was isolated from 17 PTLD, including 6 EBV-positive and 11 EBV-negative specimens. EBV status was determined by clinical EBER positivity and RefSeq testing for one sample (PTLD12). All 6 EBV-positive PTLDs (Type III latency) (Young L S & Rickinson AB (2004) Nat Rev Cancer 4(10):757-768.) were strongly positive for RNase R-resistant circBART_1&2, whereas three of the EBV-negative samples (PTLD13, PTLD15 and PTLD16) were very weakly positive. Several of these tumors had DNA available for retesting by EBV qPCR, including the three PTLD clinically reported as EBV-negative by EBER staining but positive for circBART RT-PCR (PTLD 13, 15 and 16). PTLD 13 and 15 had higher EBV genome copy numbers than EBER-positive PTLD 8 and 10 cases, suggesting false-negativity for EBER staining. PTLD 16 had <0.05 EBV genome copies/cell (see Materials and Methods for details) but retained weak circBART positivity.

C17 and C15 are two EBV-positive nasopharyngeal carcinoma xenografts that retain natively-infected latent EBV infection (Busson P, et al. (1988) Int J Cancer 42(4):599-606, Dittmer D P, et al. (2008) Int J Cancer 123(9):2105-2112); both C17 and C15 were positive for RNase R-resistant circBART PCR products, although the viral gene load for both circBART and LMP2 RNAs were substantially higher in C15 tissue. Similarly, an EBV-positive AIDS-associated lymphoma was positive for RNase R protected circBART products. In contrast, RNase R treatment diminished or eliminated linear viral (LMP2) and cellular (GAPDH) mRNA expression for the tumors.

To further confirm the circularity of circBART_1 and_2, two antisense DNA oligonucleotides were designed (ASO-BSJ1 and ASO-BSJ2) targeting the unique junction sites for BSJ1 and BSJ2 respectively. The ASOs were annealed to isolated B95-8 (negative control), Akata, sLCL and Raji RNAs. RNase H, which cleaves DNA:RNA hybrids, abolished DP1 RT-PCR positivity from Akata, sLCL and Raji RNAs but not in B95-8 RNA. GAPDH linear amplification products were not affected by RNase H treatment. RNase R treatment was also used followed by polyadenylation and poly(A)+RNA depletion (RPAD), a method for purifying circular RNAs in preference over linear RNAs (Panda A C, et al. (2017) Nucleic Acids Res 45(12):e116). RPAD treatment of Akata RNA depleted 18S ribosomal RNA (linear) relative to circBART_2 consistent with BART_2 circularization. RNase R treatment followed by polyadenylation and poly(A)+RNA depletion (RPAD) increased circBART transcripts. Relative RNA was determined by normalizing the qPCR Ct values RPAD+RNA to untreated control RNA (RPAD−).

Minor EBV-encoded backspliced junctions from BHLF1 and LMP2 were identified from several cell lines and tumors (Tables 4-7). Notably, two BSJ from the LMP2 locus (360 nt-1682 nt and 1026 nt-1682 nt) were identified by RNase R-protected sequencing of BC1 cells (Tables 4-7). On RT-PCR analysis, using DP7 and DP8 primer pairs (Table 10), multiple BSJ from presumed LMP2-encoded circular RNAs were expressed from cell lines (Akata and B95-8) and C15, AIDS-associated lymphoma and PTLD9.

For EBV circRNA expression following lytic induction, EBV positive Daudi, Akata, sLCL and B95-8 cells were treated with DMSO or NaB/TPA for 48 h. Extracted RNA was analyzed by RT42 PCR using junction spanning divergent primers for circBART (DP1) and circBHLF1. Viral LMP2 and cellular β-actin linear 43 transcripts were analyzed as internal controls using convergent primers. DP1 RT-PCR amplified circBART-BSJ1 and BSJ2 in all conditions except B95-8 which has a deletion in BART locus. CircBHLF1 BSJ-PCR product (~200bp), was detected in NaB/TPA treated Akata and B95-8. Daudi is a Burkitt's lymphoma cell line which has a deletion in BHLF1 and its promoter region.

For the circBHLF1 and circLMP2 expression in different cell lines, CIRI2 predicted additional EBV circRNAs in BC1 (Tables 4-7). RNase R treated (+) or untreated (−) 50 RNAs from cell lines having various forms of EBV latency, were analyzed by RT-PCR using divergent primers spanning BSJs in circBHLF1, circLMP2 and convergent primers for linear LMP2 and GAPDH transcripts. Sequencing analysis of the circBHLF1-BSJ spanning PCR product confirmed the predicted junction site given in Table 10. To confirm the predicted BSJ sites for circLMP2 DP7 was used for RT-PCR (Table 10) which produced multiple PCR products ranging between 200-1,200 bp enriched following RNase R treatment with Akata and B95-8 RNA. Following sequencing analysis of the PCR products an additional junction between 58nt-1682 nt was found in Mutu strain genome position which was validated by circLMP2 DP8 primers.

For the circBHLF1 and circLMP2 expression in tumor samples. RNase R treated (+) or untreated (−) RNAs from EBV(+) PTLD9, EBV(−) PTLD7, NPC tumor lines C17, C15 and an EBV (+) AIDS associated lymphoma, were used for RT-PCR with DP2 primers to detect circBARTs, circBHLF1 (DP6) and circLMP2 (DP8). Convergent primers for LMP2 and GAPDH linear transcripts were used as internal controls and to assess RNaseR treatment efficiency.

EXAMPLE 6

This example demonstrates the sequencing of KSHV circRNAs.

RNAs from DMSO or NaB/TPA-induced KSHV-infected primary effusion lymphoma cell lines BCBL1 and BC-1 were treated with RNase R prior to RNA sequencing to search for KSHV-encoded circRNAs. CIRI2 analysis revealed numerous potential KSHV circRNAs based on backspliced junctional alignments to the BCBL1 KSHV strain (HQ404500) (Tables 8-9). Among these, a viral interferon regulatory factor 4 (vIRF4) BSJ read (87,690 nt-88, 321 nt) was detected in untreated cell lines at high levels (220-214 RPM). After lytic virus activation, the junction counts were reduced in BC1NaB/TPA from 220 to 13 RMP, and in BCBL1NaB/TPA from 214 to 27 RPM (Tables 8-9). Assessment of potential acceptor and donor splice sites in this region showed relatively high entropy scores for the formation of this BSJ, and the complete circvIRF4 was sequenced using the DP9 primer pairs anchored in exon 1 (Table 10).

CircvIRF4 maps to the N-terminus of its parent transcript: it is a 632 nucleotide intronic-exonic circRNA, with backsplicing flanking the canonical vIRF4 splice-donor site. CircvIRF4 transcripts detected in latent PEL cells were resistant to RNase R digestion in contrast to linear KSHV viral interleukin 6 (vIL6) and GAPDH mRNAs.

BSJ reads from the PAN/K7.3 locus were also found (Tables 8-9). Specific individual BSJ counts were low, however, the aggregate count of all BSJs from this region was very high. The majority of BSJs was from the complementary strand of the canonical PAN transcript, identified as K7.3 (Dresang L R, et al. (2011) BMC Genomics 12:625) and overlapped within the genome locus spanning 28198nt-29016nt (BCBL1, HQ404500) (Tables 8-9). Ten K7.3 and one PAN BSJs were found in latent BC1 and BCBL1 RNAs that would generate predicted circRNAs ~304-819 nucleotides in length (Tables 8-9). BC1 has the lowest number of circRNAs from this region. Following reactivation the number of circPAN and circK7.3 RNA backspliced junction reads increased (Tables 8-9). In BC1NaB/TPA a total of 34 circPAN/K7.3 were identified at >500 RPM, twenty of which were also found in BCBL1NaB/TPA at >50 RPM. In order to validate the circRNA prediction analysis for the PAN/K7.3 region, a divergent primer pair (DP5) was designed that binds to a common region found in the majority of the predicted circPAN and circK7.3 RNAs. RT-PCR results using DP5 generated multiple bands ranging between ~200-700 bp. The number and total intensity of these bands correlated with sequencing read counts, with BC1DMSO showing the least number of PCR products. The majority of circPAN transcripts were resistant to RNase R treatment and their levels increased, in contrast to circvIRF4, following NaB/TPA treatment (Tables 8-9). Sequencing analysis of circPAN/K7.3 PCR products cloned from BCBL1 confirmed some of the identified junctions.

CircvIRF4 and circPAN/K7.3 were detected in KSHV-positive PELs. RNAs extracted from DMSO or NaB/TPA treated KSHV positive BC1, BCBL1 and BCP1 and KSHV-negative BJAB cell lines and tested with DP3 and DP5 divergent primer RT-PCR. Nuclease-resistant circvIRF4 was present in all untreated KSHV-positive cell lines but markedly diminished after NaB/TPA induction. In contrast, circPAN/K7.3 products were detected from all KSHV-positive cell lines and markedly increased after NaB/TPA treatment. CircPAN/K7.3 banding patterns varied between cell lines and with virus induction. Viral interleukin-6 (vIL6) and cellular GAPDH mRNA RT-PCR amplification were carried out for comparison.

For the identification of KSHV RNase R-resistant RNAs, a comparison of deposited BCBL1 poly(A)$^+$-RNA sequences (SRX2323239, BCBL1$^{polyA+seq}$) and RNase R-treated RNAs from BCBL1 cells with and without sodium butyrate-phorbol ester (NaB/TPA) revealed KSHV RNase R-resistant RNAs with potential back-spliced junctions (BSJ) from KSHV circular RNAs. Two expanded views, spanning the PAN/K7.3 and the vIRF4 regions have back-splice junctions identified by CIRI2 alignment to the deposited BCBL1 HQ404500 genome (Tables 8-9). For circvIRF4 (right panel, 85,600-88,400 nt), back-splicing from a cryptic donor site in exon 2 to a cryptic acceptor site in exon 1 generates a single 632 bp RNA plasmid. For circPAN/K7.3 (28,200-29,300 nt), multiple cyclized RNAs from both sense and antisense orientations were identified by BSJ analysis (Tables 8-9). A divergent PCR primer pair (DP5) was designed to detect the most common circRNAs from this locus.

Tissues from ten KS tumors (KS1-3 having degraded RNA, as a result of freeze-thaw during extended storage, KS4-10 were obtained from AIDS and Cancer Specimen Resource) and a KSHV-positive MCD were compared to a PTLD (negative control) and BC1 (positive control) by KSHV circRNA RT-PCR. CircvIRF4 was detected in four of the ten KS tumor samples, and RNase R-resistant circPAN/K7.3 isoforms were present in MCD and six KS tumors despite diminished RNA integrity for some of the samples, as reflected by low beta-actin, LANA and v-cyclin mRNA levels. CircvIRF4 BSJ was found in three KS samples (KS4, KS6 and KS8) which also showed higher levels of LANA mRNA. Various RNase R resistant circPAN/K7.3 isoforms (~250-700bp) were detected in KS4, KS6 and KS9. BJAB and BC-1 RNAs were used as virus negative and positive controls, respectively.

For the KSHV circRNAs in KS and MCD patient tissues, RNAs extracted from three KS and one MCD show circ-PAN/K7.5 BSJ in all KSHV-positive tissues but circvIRF4-BSJ was detected in only one KS sample. The KS specimens, stored in liquid nitrogen from the mid-1990s, showed evidence of RNA degradation with absence or diminished v-cyclin and β-actin mRNA RT-PCR positivity, consistent with the notion that circRNAs are particularly resistant to degradation. PTLD (EBV-negative) and BC-1 RNAs were used as virus negative and positive controls, respectively.

To confirm the circularity of circvIRF4 an in vitro RNase H assay was performed with an ASO targeting the unique circvIRF4 junction. This abolished circvIRF4 RT-PCR positivity from BC1 and BCBL1 RNAs while control cellular GAPDH mRNA was unaffected. In vitro RNase H assays using annealed ASO showed depletion of the circvIRF4 junctional sequences after RNase H treatment for BC1 and BCBL, but not in KSHV-negative BJAB, RNAs. In addition RNase R treatment followed by RPAD reduced linear 18S RNA did not significantly reduce circvIRF4 RNA levels.

In addition to circvIRF4 and circPAN/K7.3, a KSHV BSJ from the miRNA locus (Tables 8-9) was detected by RT-PCR only in BC1NaB/TPA RNA, but not other cell lines, and was not further explored. In NaB/TPA treated BC1 and BCBL1 cells, additional candidate BSJ reads were found at low abundance from K4, ORF49, ORF69, K12, ORF71, ORF72 and from newly described transcripts K1.3, K4.5, K4.7, K12.5 (Tables 8-9).

TABLE 8

BC1-DMSO

| circRNA_ID | circRNA_start | circRNA_end | strand | #junction_reads | SM_MS_SMS |
|---|---|---|---|---|---|
| HQ404500.1: 87690\|88321 | 87690 | 88321 | - | 95 | 29_32_4 |
| HQ404500.1: 28273\|28593 | 28273 | 28593 | - | 2 | 1_2_0 |
| HQ404500.1: 28290\|28593 | 28290 | 28691 | - | 2 | 1_2_0 |
| HQ404500.1: 28519\|29016 | 28519 | 29016 | - | 5 | 1_3_0 |
| HQ404500.1: 117854\|122054 | 117854 | 122054 | - | 36 | 7_11_7 |
| HQ404500.1: 117854\|122169 | 117854 | 122169 | - | 202 | 54_81_30 |

| circRNA_ID | #non_junction_reads | junction_reads_ratio | gene_id | RPM |
|---|---|---|---|---|
| HQ404500.1: 87690\|88321 | 95 | 0.659 | vIRF4 | 220.467251 |
| HQ404500.1: 28273\|28593 | 2088 | 0.002 | K7.3 | 4.64141582 |
| HQ404500.1: 28290\|28593 | 2393 | 0.002 | K7.3 | 4.64141582 |
| HQ404500.1: 28519\|29016 | 3423 | 0.003 | K7.3 | 11.6035395 |
| HQ404500.1: 117854\|122054 | 6517 | 0.011 | miRNA cluster | 83.5454847 |
| HQ404500.1: 117854\|122169 | 6648 | 0.058 | miRNA cluster | 468.782998 |

TABLE 9

BCBL1-DMSO

| circRNA_ID | circRNA_start | circRNA_end | strand | #junction_reads | SM_MS_SMS |
|---|---|---|---|---|---|
| HQ404500.1: 87690\|88321 | 87690 | 88321 | - | 33 | 15_20_2 |

TABLE 9-continued

| BCBL1-DMSO | | | | | |
|---|---|---|---|---|---|
| HQ404500.1:28198\|29016 | 28198 | 29016 | − | 10 | 1_10_0 |
| HQ404500.1:28273\|28691 | 28273 | 28691 | − | 9 | 4_5_1 |
| HQ404500.1:28406\|29044 | 28406 | 29044 | + | 7 | 3_3_0 |
| HQ404500.1:28273\|28593 | 28273 | 28593 | − | 6 | 1_5_0 |
| HQ404500.1:28692\|29016 | 28692 | 29016 | − | 6 | 4_6_0 |
| HQ404500.1:28273\|28624 | 28273 | 28624 | − | 4 | 2_3_0 |
| HQ404500.1:28273\|28614 | 28273 | 28614 | − | 2 | 1_2_0 |
| HQ404500.1:28273\|29016 | 28273 | 29016 | − | 2 | 0_2_1 |
| HQ404500.1:28290\|28593 | 28290 | 28593 | − | 2 | 2_1_0 |
| HQ404500.1:28290\|28691 | 28290 | 28691 | − | 4 | 1_2_0 |
| HQ404500.1:28519\|29016 | 28519 | 29016 | − | 2 | 2_2_0 |

| circRNA_ID | #non_junction_reads | junction_reads_ratio | gene_id | RPM |
|---|---|---|---|---|
| HQ404500.1:87690\|88321 | 154 | 0.294 | vIRF4 | 214.146658 |
| HQ404500.1:28198\|29016 | 2725 | 0.007 | K7.3 | 64.8929267 |
| HQ404500.1:28273\|28691 | 6837 | 0.003 | K7.3 | 58.403634 |
| HQ404500.1:28406\|29044 | 14141 | 0.001 | PAN | 45.4250487 |
| HQ404500.1:28273\|28593 | 7031 | 0.002 | K7.3 | 38.935756 |
| HQ404500.1:28692\|29016 | 6954 | 0.002 | K7.3 | 38.935756 |
| HQ404500.1:28273\|28624 | 6505 | 0.001 | K7.3 | 25.9571707 |
| HQ404500.1:28273\|28614 | 6455 | 0.001 | K7.3 | 12.9785853 |
| HQ404500.1:28273\|29016 | 4855 | 0.001 | K7.3 | 12.9785853 |
| HQ404500.1:28290\|28593 | 8088 | 0.000 | K7.3 | 12.9785853 |
| HQ404500.1:28290\|28691 | 8045 | 0.001 | K7.3 | 25.9571707 |
| HQ404500.1:28519\|29016 | 12493 | 0.000 | K7.3 | 12.9785853 |

EXAMPLE 7

This example demonstrates the subcellular localization of viral circRNAs.

To functionally characterize these viral circRNAs, nuclear and cytoplasmic fractions of dually-infected BC-1 cells were isolated. EBV circBART_1.1 and circBART_2.1, having a retained intron between exon Ma and IIIb, were detected in the nuclear fraction, whereas entirely exonic circBART_1.2 and circBART_2.2 and circvIRF4 were detected in both nuclear and cytoplasmic fractions. RNA extracted from nuclear (Nuc) and cytoplasmic (Cyto) fractions of the KSHV and EBV co-infected BC1 cell line was either treated (+) or untreated (−) with RNase R. B SJ spanning PCR products from intron-retaining circBART_1.1 and circBART_2.1 were detected mainly in the nuclear fraction. Exonic circBART_1.2 and circBART_2.2 were found in both fractions. CircvIRF4 junction spanning PCR products were detected in both fractions. Protein immunoblotting for lamin A/C (nuclear) and LAMP1 (cytoplasmic) was used to confirm fractionation quality.

To determine whether the cytoplasmic viral circRNAs were associated with the cellular translation machinery, polysome fractionation was performed. qRT-PCR analysis of polysome fractions revealed that both KSHV circvIRF4 and EBV circBART BSJ1 and BSJ2 partitioned to untranslated fractions (fractions 2-4) whereas cellular and viral mRNAs were enriched in the polysome fractions (fractions 10-12). CircvIRF4, circBART1 and 2 RNAs were not preferentially detected in polysomal fractions but mRNAs for translated v-cyclin, LMP2 and GAPDH proteins preferentially fractionated with polysomes. RNA detection was determined by qRT-PCR for each RNA.

EXAMPLE 8

This example demonstrates the identification of cellular circular RNAs in EBV/KSHV infected tumors and cell lines.

In total, 30,178 human circRNAs were predicted with at least two backspliced junction reads in all PTLD and lymphoma cell lines sequenced. Approximately 11% of these (1,385) were shared by all four samples but notably, the majority of predicted circRNAs were not overlapping. In part, this may reflect the cellular heterogeneity found within PTLDs (e.g. tumor infiltrating macrophages and T cells). 35 and 40 novel circRNAs were found that were exclusively detected in EBV-positive and EBV-negative PTLDs respectively. A total of 22,276 and 13,641 human circRNA BSJs were found in DMSO- and NaB/TPA-treated BJAB, BC1 and BCBL1 cell lines. 5.3% (1182) of the human circRNAs from the DMSO-and 3.7% (505) of the human circRNAs from the NaB/TPA-treated samples were only found in KSHV infected PELs. 371 novel cellular circRNAs were identified in latent and lytic KSHV-positive PELs.

For the type of predicted human circRNAs in PTLD samples, CIRI2 analysis found a total of 5178, 4602, 5361 and 6138 human circRNAs in PTLD 4,5,6 and 9 respectively. ~90% of these are exonic and the rest are generated from intronic and intergenic regions of the human genome. EBV (+) PTLD 6 and 9 express 455 human circRNAs in common and 35 of them were identified in this study. EBV (−) PTLD 4 and 5 express 303 human circRNAs in common and 40 new circRNAs were found in this group. ~99% of circRNAs (1385) that are common in all samples were annotated in circBase.

For the type of predicted human circRNAs in KSHV (+/−) cell lines, CIRI2 analysis found a range of 4,100 to 14,400 cellular circRNAS these cell lines. 273 new human circRNAs were found both in latent BC1 and BCBL1 samples. NaB/TPA treated PEL cells have 505 human circRNAs in common, 98 of which have not been previously reported.

TABLE 10

| Name<br>Divergent primers | Sequence | SEQ ID NO: | PCR product size (bp) |
|---|---|---|---|
| Primers and antisense oligos (ASO) used in this study ||||
| DP1<br>(circBART.BSJ2) | CGCCCGTATTCACACATTCC | 1 | 160-264 |
| | GACGCTAGTGCTGCATGGG | 2 | |
| DP2<br>(circBART) | AGCCCTTCTTCGTTATGCAC | 4 | 400-700 |
| | TGAGGAATACCTCGTTGTCTTCCG | 3 | |
| DP3<br>(circIRF4) | CAAAGCTACGAGGAGGCAGG | 30 | 577 |
| | CGCCGACACCAACGCATCAAAC | 31 | |
| DP4<br>(circIRF4) | GGCGATATAACGACTGAACAGA | 32 | 139 |
| | CAAATGCATGGTACACCGAATAC | 5 | |
| DP5<br>(circPAN/K7.3) | CGCCCACTGGTGTATCAGA | 33 | 126-668 |
| DP6<br>(circBHLF1) | CGCTTGCCTGGTCCTGG | 35 | 216 |
| | CAGGCGTACCGGGCCAG | 36 | |
| DP7<br>(circLMP2) | CACCAGCGATTAGCGCG | 37 | 210-1,178 |
| | GGTCATTAGATGCTGCCGCTAC | 38 | |
| DP8<br>(circLMP2) | GCAGCGGCATATGAGCTGG | 39 | 258 |
| | GGTCATTAGATGCTGCCGCTAC | 40 | |
| DP9<br>(circIRF4) | CATTTGATGAGGAGTGTGATAGAG | 41 | 632 |
| | GAACCGCTATTACAATGTTGGC | 6 | |
| DP10<br>(circPAN/K7.3) | TTCTGTGTTTGTCTGATTCTTAG | 42 | 325-744 |
| | CCGAAACAACGAATGAGCA | 43 | |
| DP11<br>(circBART.BSJ1) | GGTCAAGTAGCTGCGTCCAAA | 44 | 117 |
| | GACGCTAGTGCTGCATGGG | 2 | |
| Cnvergent primers used for RT-PCR and qPCR ||||
| GAPDH.F | GTCATCAATGGAAATCCCATCACC | 45 | 320 |
| GAPDH.R | TGAGTCCTTCCACGATACCAAA | 46 | |
| GAPDH.F | TGCACCACCAACTGCTTAGC | 47 | 98 |
| GAPDH.R | GGCATGGACTGTGGTCATGAG | 48 | |
| Beta-actin.F | CACACTGTGCCCATCTATGAGG | 49 | 191 |
| Beta-actin.R | TCGAAGTCTAGGGCGACATAGC | 50 | |
| 18S.F | CGAACGTCTGCCCTATCAACTT | 51 | 115 |
| 18S.R | TGTGGTAGCCGTTTCTCAGG | 52 | |
| vIL6.F | TTCAAAACACGCACCGCTTG | 53 | 210 |
| vIL6.R | AAACGTGGACGTCATGGAGC | 54 | |
| v-cyc.F | CGCCTGTAGAACGGAAACAT | 55 | 137 |
| v-cyc.R | TTGCCCGCCTCTATTATCAG | 56 | |
| LANA F | TTTAGTGTAGAGGGACCTTGGG | 57 | 258 |
| LANA R | TCTCCATCTCCTGCATTGCC | 58 | |
| KSHV.ORF50.F | CAGAGTCTATTCGCCCTGTTAG | 59 | 115 |
| KSHV.ORF50.R | CTGGTACAGTCCTTGCAGAATA | 60 | |
| KSHV.K8.F | CCAAGAGGCGACTACATAGAAAG | 61 | 111 |
| KSHV.K8.R | GGGTGATGTTCCCTACCTTAAC | 62 | |
| KSHV.ORF37.F | TGGGCGAGTTTATTGGTAGTG | 63 | 125 |
| KSHV.ORF37.R | CGCTGATGTGCGTTCATTTG | 64 | |

TABLE 10-continued

| Name<br>Divergent primers | Sequence | SEQ ID NO: | PCR product<br>size (bp) |
|---|---|---|---|
| KSHV.ORF39.F | CAGGCAGCAGTAGAATCAGATAA | 65 | 110 |
| KSHV.ORF39.R | GACGGTCGTGTGGTACATAAA | 66 | |
| LMP2.F | TGCCTGCCTGTAATTGTTGCG | 67 | 151 |
| LMP2.R | GCAGCGGCATATGAGCTGG | 68 | |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, $T_m$ is defined as:

$$Tm = 81.5 + 16.6 \log_{10}\left(\frac{[Na+]}{1.0 + 0.7[Na^+]}\right) + 0.41\,(\%[G+C]) - \frac{500}{n} - P - F$$

Where Tm=melting temperature in ° C.
[Na$^+$]=Molar concentration of sodium ions in
%[G+C]=percent of G+C bases in DNA sequence
n=length of DNA sequence in bases
P=temperature correction for % mismatched base pairs (~1° C. per 1% mismatch)
F=correction for formamide concentration (=0.63° C. per 1% [formamide])

With reference to the definition of "Tm" above, as used herein, "high stringency" hybridization conditions include a NaCl content of from 0.0165M to about 0.0330M at a temperature of about 5° C. to 10° C. below Tm.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preparing a sample of specifically hybridized γ-herpesvirus circRNA, the method comprising:
   obtaining a tissue or fluid sample from a subject and specifically hybridizing one or more oligonucleotides to γ-herpesvirus circRNA (i) in the tissue or fluid sample from the subject or (ii) extracted from the tissue or fluid sample from the subject, thereby preparing a sample of specifically hybridized γ-herpesvirus circRNA.

2. The method of claim 1, wherein RNA is extracted from the tissue sample.

3. The method of claim 1, wherein the one or more oligonucleotides are specifically hybridized to γ-herpesvirus circRNA in situ.

4. The method of claim 1, wherein prior to specifically hybridizing the one or more oligonucleotides to the γ-herpesvirus circRNA, the tissue or fluid sample, or RNA extracted therefrom, is first subjected to treatment with an RNAse.

5. The method of claim 1, wherein specifically hybridizing the one or more oligonucleotides to the γ-herpesvirus circRNA comprises rtPCR.

6. The method of claim 1, wherein the γ-herpesvirus is Epstein-Barr Virus (EBV).

7. The method of claim 1, wherein the γ-herpesvirus is Kaposi's Sarcoma-Associated Herpesvirus (KSHV).

8. A method comprising obtaining a tissue or fluid sample from a subject and assaying the tissue or fluid sample to determine the presence of y-herpesvirus circRNA,
   wherein the method for detecting the presence of y-herpesvirus circRNA is rtPCR,
   wherein the rtPCR employs, as primer pairs, oligonucleotides having the following sequences: (a) DP1-R (reverse): CGCCCGTATTCACACATTCC (SEQ ID NO:1) and DP1-F (forward): GACGCTAGTGCTG-CATGGG (SEQ ID NO:2), (b) DP2-F (forward): TGAGGAATACCTCGTTGTCTTCCG (SEQ ID NO:3) and DP2-R (reverse):

AGCCCTTCTTCGTTATGCAC (SEQ ID NO:4) or (c) circvIRF4-R (reverse): CAAATGCATGGTACACCGAATAC (SEQ ID NO:5) and circvIRF4-F (forward): GAACCGCTATTACAATGTTGGC (SEQ ID NO:6).

9. A method of preparing a sample of specifically hybridized viral circRNA from a double-stranded DNA virus, the method comprising;
   obtaining a tissue or fluid sample from a mammalian subject; and
   specifically hybridizing one or more oligonucleotides to viral circRNA from a double- stranded DNA virus (i) in the tissue or fluid sample from the subject or (ii) extracted from the tissue or fluid sample from the subject, thereby preparing a sample of specifically hybridized viral circRNA from a double-stranded DNA virus.

10. The method of claim 9, wherein RNA is extracted from the tissue sample.

11. The method of claim 9, which distinguishes between viral circRNA and linear viral RNA.

12. The method of claim 9, which involves pretreatment of the tissue or fluid sample, or extracted RNA, with RNAse R.

13. The method of claim 9, which comprises using divergent reverse transcription PCR (rtPCR).

14. A method of determining the presence of γ-herpesvirus circRNA in a subject and treating a condition associated with y-herpesvirus infection in the subject, the method comprising:
   receiving an identification of a subject as having γ-herpesvirus circRNA in a tissue or fluid sample from the subject, wherein γ-herpesvirus circRNA has been detected by a method comprising obtaining a tissue or fluid sample from the subject and assaying the tissue or fluid sample to determine the presence of γ-herpesvirus circRNA; and
   administering an oligonucleotide to the subject identified as having γ-herpesvirus circRNA in the tissue or fluid sample from the subject, wherein the oligonucleotide that hybridizes to the BART small junction (Si) sequence (TCGACGGGCAAGGTCCGGCGTGTC (SEQ ID NO:7)), the BART large junction (LI) sequence (TCGACGGGCAAGATGCCATTGGGC (SEQ ID NO:8)), or the RF junction sequence (CATCTACCTCAGCCCCCGCGCCCC (SEQ ID NO:13).

15. The method of claim 14, wherein RNA is extracted from the tissue sample, and then the extracted RNA is assayed to determine the presence of γ-herpesvirus circRNA.

16. The method of claim 14, wherein the fluid sample or tissue is assayed to determine the presence of y-herpesvirus circRNA in situ.

17. The method of claim 14, wherein prior to assaying the tissue or fluid sample or RNA extracted therefrom to determine the presence of γ-herpesvirus circRNA, the tissue or fluid sample, or RNA extracted therefrom, is first subjected to treatment with an RNAse.

18. The method of claim 14, wherein the method for detecting the presence of γ-herpesvirus circRNA is rtPCR.

19. The method of claim 14, wherein the y-herpesvirus is Epstein-Barr Virus (EBV).

20. The method of claim 14, wherein the y-herpesvirus is Kaposi's Sarcoma-Associated Herpesvirus (KSHV).

21. The method of claim 18, wherein the rtPCR employs, as primer pairs, oligonucleotides having the following sequences: (a) DP1-R (reverse):
   CGCCCGTATTCACACATTCC (SEQ ID NO:1) and DP1-F (forward):
   GACGCTAGTGCTGCATGGG (SEQ ID NO:2), (b) DP2-F (forward):
   TGAGGAATACCTCGTTGTCTTCCG (SEQ ID NO:3) and DP2-R (reverse):
   AGCCCTTCTTCGTTATGCAC (SEQ ID NO:4) or (c) circvIRF4-R (reverse):
   CAAATGCATGGTACACCGAATAC (SEQ ID NO:5) and circvIRF4-F (forward):
   GAACCGCTATTACAATGTTGGC (SEQ ID NO:6).

22. The method of claim 8, wherein the γ-herpesvirus is Epstein-Barr Virus (EBV).

* * * * *

UNITED STATES PATENT AND TRADEMARK OFFICE
CERTIFICATE OF CORRECTION

PATENT NO. : 11,512,357 B2
APPLICATION NO. : 17/059949
DATED : November 29, 2022
INVENTOR(S) : Patrick S. Moore et al.

It is certified that error appears in the above-identified patent and that said Letters Patent is hereby corrected as shown below:

In the Claims

Column 63, Claim 3, replace "in situ" with "*in situ*".

Column 63, Claim 4, replace "y-herpesvirus" with "γ-herpesvirus".

Column 64, Claim 8, Line 58, replace "y-herpesvirus" with "γ-herpesvirus".

Column 64, Claim 8, Line 59, replace "y-herpesvirus" with "γ-herpesvirus".

Column 64, Claim 8, replace "rtPCR," with "rtPCR, and".

Column 65, Claim 9, replace "comprising;" with "comprising:".

Column 65, Claim 14, Line 29, replace "y-herpesvirus" with "γ-herpesvirus".

Column 65, Claim 14, replace "(Si)" with "(SJ)".

Column 66, Claim 14, replace "(LI)" with "(LJ)".

Column 66, Claim 16, replace "y-herpesvirus" with "γ-herpesvirus".

Column 66, Claim 16, replace "in situ" with "*in situ*".

Column 66, Claim 19, replace "y-herpesvirus" with "γ-herpesvirus".

Column 66, Claim 20, replace "y-herpesvirus" with "γ-herpesvirus".

Signed and Sealed this
Twenty-first Day of February, 2023

Katherine Kelly Vidal
*Director of the United States Patent and Trademark Office*